(12) United States Patent
Bell et al.

(10) Patent No.: US 6,361,998 B1
(45) Date of Patent: Mar. 26, 2002

(54) EFFICIENT CULTURE OF STEM CELLS FOR THE PRODUCTION OF HEMOGLOBIN

(75) Inventors: David N. Bell, Oakville; Kathryn Emma Matthews, Toronto; Susan G. Mueller, Milton, all of (CA)

(73) Assignee: Hemosol Inc., Mississauga (CA)

( * ) Notice: Subject to any disclaimer, the term of this patent is extended or adjusted under 35 U.S.C. 154(b) by 0 days.

(21) Appl. No.: 09/339,838

(22) Filed: Jun. 25, 1999

(51) Int. Cl.$^7$ .......................... C12N 5/00; C12N 15/00; C12P 21/06; C12P 21/04; C07K 1/00
(52) U.S. Cl. ...................... 435/407; 435/69.1; 435/325; 435/70.1; 435/405; 530/350; 536/23.5
(58) Field of Search .............................. 435/325, 69.1, 435/405, 407, 70.1; 530/350; 536/23.5

(56) References Cited

U.S. PATENT DOCUMENTS

| | | | |
|---|---|---|---|
| 5,292,654 A | | 3/1994 | Yoshimura et al. ....... 435/240.2 |
| 5,397,706 A | * | 3/1995 | Correa et al. .......... 435/240.31 |
| 5,945,337 A | * | 8/1999 | Brown ...................... 435/389 |

FOREIGN PATENT DOCUMENTS

EP        0786519    *    7/1997

OTHER PUBLICATIONS

J. Rudinger, "Peptide Hormones", Edited by Parsons, University Park Press, Baltimore, p. 1–17, Jun. 1976.*
Durand, B., et al., 1993, Leukemia and Lymphoma, 11 (3–4), 263–73.
Migliaccio, G. and Migliaccio, A.R., 1987, British J. Of Haemotology, vol. 67, No. 2, 129–133.
Mobest et al., 1995, Experimental Hematology, vol. 23, No. 8, p. 908.
Sandstrom, C.E. et al., 1995, Blood, 86(3), 958–70.
Glimm, H. et al., 1998, Human Gene Therapy, vol. 9, p. 771–778.
Mobest et al., Biotechnology and Bioengineering, vol. 60(3), p. 341–347, Nov. 1998.*
Iscove et al., Experimental Cell Research, vol. 126, p. 121–126, 1980.*
Kralovics et al., Blood, vol. 90(5), p. 2057–2061, Sep. 1997.*
D'Andrea et al. (1989) Cell 57: 277.
Winkelmann et al (1990) Blood 76: 24.
Jones et al (1990) Blood 76: 31.
Yoshimura et al (1990) Nature 348:647.
Klingmuller et al (1995) Cell 80: 729–738.
D'Andrea (1991) Mol Cell Biol 11: 1980.
Kirby et al (1996) Proc Natl Acad Sci 93: 9402.
Watowich et al (1994) Mol Cell Biol 14: 3535.
Longmore et al (1994) Mol Cell Biol 14: 2266–2277.
Pharr et al (1993) Proc Natl Acad Sci 90: 938.
Pharr et al (1994) Proc Natl Acad Sci 91: 7482.
Kralovics et al (1997) Blood 90: 2057–2061.
Iscove et al (1980) Exp. Cell Res. 126: 121–126.
Polini et al (1997) Hematol. Cell Ther. 39:49–58.
Fibach et al (1991) Int. J. Cell Cloning 9:57–64.
Lansdorp and Dragowska (1992) J. Exp. Med. 175: 1501–1509.
Malik et al (1998), Blood 91:2664–2671.
Grandchamp B et al (1985) J Biol. Chem. 260:9630–5.
Battistini et al (1991) 78:2098–2103.
Kawasaki et al (1996) Arch Biochem Biophys 328:289–94.
Fibach et al (1995) Blood 85:2967–2974.
Beru et al (1983) J. Cell. Biochem. 21:93–105.
Ebert et al (1981) Cancer Res 41:937–41.
Muta and Krantz (1995) J Cell Physiol.163: 38–50.
Migliaccio (1992) Blood 79:2620.
Schmid et al (1991) J. Biotechnol. 17(2):155 (abstract).
Lebkowski et al (1995) Stem Cells 13:607–612.
Munshi et al (1993) 67(1):562.
Toneguzzo and Keating (1986) Mol. Cell. Biol. 6:703–706.
Piao et al (1996) PNAS USA 93(25):14665 (abstract).
Narayanan et al (1989) Exp. Hematol. 17:832–835.
Takahashi et al (1992) Leuk. Res. 761–767.
Chomczymski (1987) Anal. Biochem. 162:156.

* cited by examiner

Primary Examiner—Deborah J. R. Clark
Assistant Examiner—Shin-Lin Chen
(74) Attorney, Agent, or Firm—Bereskin & Parr; Micheline Gravelle

(57) ABSTRACT

The present invention describes a serum-free medium that promotes the growth and differentiation of erythroid cells, cells that are highly transducible by a non-viral method and genes which increase the growth of erythroid cells and decrease their dependency on Epo. This invention can be used in the expansion of hematopoietic stem cells to produce cultures of erythroid cells as a source of erythroid-specific proteins such as hemoglobin. Hematopoietic stem cells are cultured ex vivo in a serum-free culture medium with the addition of IL-3, SCF and EPO. Cells transfected with the gene described in the present invention can be cultured in the serum-free culture medium with decreased dependency on Epo and other cytokines, thereby reducing the cost of the production of hemoglobin.

15 Claims, 12 Drawing Sheets

FIGURE 1
A.
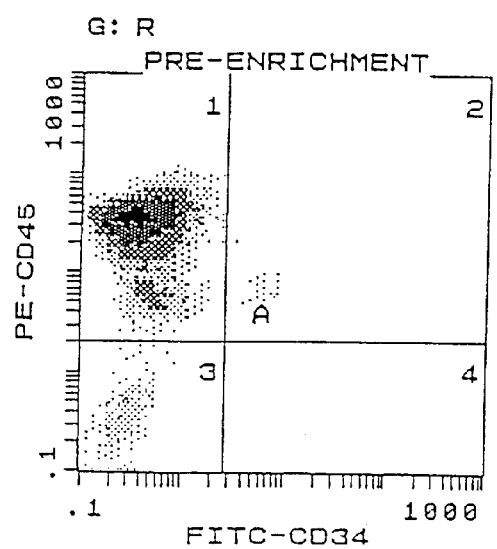
B.
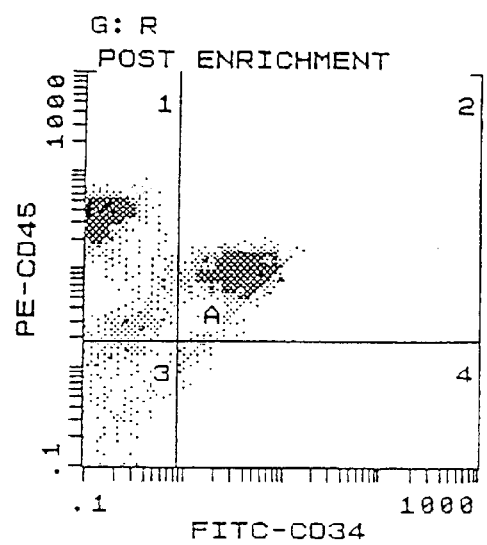

| | | | |
|---|---|---|---|
| A | 500 ng of hemoglobin | 1 | day 17 cells |
| B | 400 ng | 2 | day 17 + hemin |
| C | 300 ng | 3 | day 22 cells |
| D | 200 ng | 4 | day 22 + hemin |
| E | 100 ng | | |

| Sample | day of harvest for Western Blot | % of cells BZ+'ve on day of harvest | % of cells GlyA +'ve on day of harvest | pg of Hb / cell | pg of Hb / BZ+'ve cell |
|---|---|---|---|---|---|
| EPSFM (no hemin) | 17 | 30.3 | 52.7 | 2.3 | 7.6 |
| EPSFM, addition of 25 uM hemin at day 9 | 17 | 39.7 | 58.8 | 4.9 | 12.4 |
| EPSFM (no hemin) | 22 | 58.1 | 79.9 | 3.7 | 6.3 |
| EPSFM, addition of 25 uM hemin at day 17 | 22 | 50.8 | 70.5 | 3.8 | 7.5 |

Relative fold expansion (RFE) of CD34+ cells in liquid culture

FIGURE 9A

SEQ.ID.NO. 4
cDNA Sequence for EpoR (t439)

atggaccacctcggggcgtccctctggccccaggtcggctcccttttgtctcctgctcgctggggccgcct
gggcgcccccgcctaacctcccggaccccaagttcgagagcaaagcggccttgctggcggcccggg
ggcccgaagagcttctgtgcttcaccgagcggttggaggacttggtgtgtttctgggaggaagcggcga
gcgctggggtgggcccgggcaactacagcttctcctaccagctcgaggatgagccatggaagctgtgt
cgcctgcaccaggctcccacggctcgtggtgccgtacgcttctggtgttcgctgcctacagccgacacgt
cgagcttcgtgcccctagagttgcgcgtcacagcagcctccggcgctccgcgatatcaccgtgtcatcc
acatcaatgaagtagtgctcctagacgcccccgtggggctggtggcgcggttggctgacgagagcgg
ccacgtagtgttgcgctggctcccgccgcctgagacacccatgacgtctcacatccgctacgaggtgg
acgtctcggccggcaacggcgcagggagcgtacagagggtggagatcctggagggccgcaccga
gtgtgtgctgagcaacctgcggggccggacgcgctacaccttcgccgtccgcgcgcgtatggctgagc
cgagcttcggcggcttctggagcgcctggtcggagcctgtgtcgctgctgacgcctagcgacctggacc
ccctcatcctgacgctctccctcatcctcgtggtcatcctggtgctgctgaccgtgctcgcgctgctctccca
ccgccgggctctgaagcagaagatctggcctggcatcccgagcccagagagcgagtttgaaggcct
cttcaccacccacaagggtaacttccagctgtggctgtaccagaatgatggctgcctgtggtggagccc
ctgcaccccttcacggaggacccacctgcttccctggaagtcctctcagagcgctgctggggacga
tgcaggcagtggagccggggacagatgatgagggcccctgctggagccagtgggcagtgagcat
gcccaggatacctatctggtgctggacaaatggttgctgccccggaacccgcccagtgaggacctccc
agggcctggtggcagtgtggacatagtggccatggatgaaggctcagaagcatcctcctgctcatctgc
tttggcctcgaagcccagcccagagggagcctctgctgccagctttgagtacactatcctggaccccag
ctcccagctcttgcgtccatag

FIGURE 9B

SEQ.ID.NO. 5
Protein Sequence for EpoR (t439)

MDHLGASLWPQVGSLCLLLAGAAWAPPPNLPDPKFESKAALLAARGPEELLCFTER
LEDLVCFWEEAASAGVGPGNYSFSYQLEDEPWKLCRLHQAPTARGAVRFWCSLP
TADTSSFVPLELRVTAASGAPRYHRVIHINEVVLLDAPVGLVARLADESGHVVLRWL
PPPETPMTSHIRYEVDVSAGNGAGSVQRVEILEGRTECVLSNLRGRTRYTFAVRAR
MAEPSFGGFWSAWSEPVSLLTPSDLDPLILTLSLILVVILVLLTVLALLSHRRALKQKI
WPGIPSPESEFEGLFTTHKGNFQLWLYQNDGCLWWSPCTPFTEDPPASLEVLSER
CWGTMQAVEPGTDDEGPLLEPVGSEHAQDTYLVLDKWLLPRNPPSEDLPGPGGS
VDIVAMDEGSEASSCSSALASKPSPEGASAASFEYTILDPSSQLLRP*

FIGURE 10A

SEQ.ID.NO. 6
cDNA Sequence for EpoR(t439; R154C)

atggaccacctcggggcgtccctctggccccaggtcggctccctttgtctcctgctcgctggggccg
cctgggcgccccgcctaacctcccggaccccaagttcgagagcaaagcggccttgctggcgg
cccggggcccgaagagcttctgtgcttcaccgagcggttggaggacttggtgtgtttctgggagg
aagcggcgagcgctggggtgggcccgggcaactacagcttctcctaccagctcgaggatgagc
catggaagctgtgtcgcctgcaccaggctcccacggctcgtggtgccgtacgcttctggtgttcgct
gcctacagccgacacgtcgagcttcgtgccccctagagttgcgcgtcacagcagcctccggcgctc
cgcgatatcaccgtgtcatccacatcaatgaagtagtgctcctagacgcccccgtggggctggtg
gcatgcttggctgacgagagcggccacgtagtgttgcgctggctcccgccgcctgagacacccat
gacgtctcacatccgctacgaggtggacgtctcggccggcaacggcgcagggagcgtacaga
gggtggagatcctggagggccgcaccgagtgtgtgctgagcaacctgcggggccggacgcgct
acaccttcgccgtccgcgcgcgtatggctgagccgagcttcggcggcttctggagcgcctggtc
ggagcctgtgtcgctgctgacgcctagcgacctggaccccctcatcctgacgctctccctcatcctc
gtggtcatcctggtgctgctgaccgtgctcgcgctgctctcccaccgccgggctctgaagcagaag
atctggcctggcatcccgagcccagagagcgagtttgaaggcctcttcaccacccacaagggta
acttccagctgtggctgtaccagaatgatggctgcctgtggtggagcccctgcaccccttcacgg
aggacccacctgcttccctggaagtcctctcagagcgctgctgggggacgatgcaggcagtgga
gccggggacagatgatgagggccccctgctggagccagtgggcagtgagcatgcccaggata
cctatctggtgctggacaaatggttgctgccccggaacccgcccagtgaggacctcccagggcct
ggtggcagtgtggacatagtggccatggatgaaggctcagaagcatcctcctgctcatctgctttg
gcctcgaagcccagcccagagggagcctctgctgccagctttgagtacactatcctggaccccca
gctcccagctcttgcgtccatag

FIGURE 10B

SEQ.ID.NO. 7

Protein Sequence for EpoR (t439; R154C)

MDHLGASLWPQVGSLCLLLAGAAWAPPPNLPDPKFESKAALLAARG
PEELLCFTERLEDLVCFWEEAASAGVGPGNYSFSYQLEDEPWKLCR
LHQAPTARGAVRFWCSLPTADTSSFVPLELRVTAASGAPRYHRVIHIN
EVVLLDAPVGLVACLADESGHVVLRWLPPPETPMTSHIRYEVDVSAG
NGAGSVQRVEILEGRTECVLSNLRGRTRYTFAVRARMAEPSFGGFW
SAWSEPVSLLTPSDLDPLILTLSLILVVILVLLTVLALLSHRRALKQKIWP
GIPSPESEFEGLFTTHKGNFQLWLYQNDGCLWWSPCTPFTEDPPAS
LEVLSERCWGTMQAVEPGTDDEGPLLEPVGSEHAQDTYLVLDKWLL
PRNPPSEDLPGPGGSVDIVAMDEGSEASSCSSALASKPSPEGASAA
SFEYTILDPSSQLLRP*

SEQUENCE LISTING

<160> NUMBER OF SEQ ID NOS: 11

<210> SEQ ID NO 1
<211> LENGTH: 26
<212> TYPE: DNA
<213> ORGANISM: Homo sapiens

<400> SEQUENCE: 1
ggaagcttat ggaccacctc ggggcg            26

<210> SEQ ID NO 2
<211> LENGTH: 29
<212> TYPE: DNA
<213> ORGANISM: Homo sapiens

<400> SEQUENCE: 2
gctctagact aagagcaagc cacatagct            29

<210> SEQ ID NO 3
<211> LENGTH: 29
<212> TYPE: DNA
<213> ORGANISM: Homo sapiens

<400> SEQUENCE: 3
gctctagact atggacgcaa gagctggga            29

<210> SEQ ID NO 4
<211> LENGTH: 1317
<212> TYPE: DNA
<213> ORGANISM: Homo sapiens
<220> FEATURE:

```
<221> NAME/KEY: CDS
<222> LOCATION: (1)..(1317)
<223> OTHER INFORMATION:
<221> NAME/KEY: terminator
<222> LOCATION: (1315)..(1317)
<223> OTHER INFORMATION:

<400> SEQUENCE: 4
```

| | | | | | | | | | | | | | | | | |
|---|---|---|---|---|---|---|---|---|---|---|---|---|---|---|---|---|
| atg | gac | cac | ctc | ggg | gcg | tcc | ctc | tgg | ccc | cag | gtc | ggc | tcc | ctt | tgt | 48 |
| Met | Asp | His | Leu | Gly | Ala | Ser | Leu | Trp | Pro | Gln | Val | Gly | Ser | Leu | Cys | |
| 1 | | | | 5 | | | | | 10 | | | | | 15 | | |
| ctc | ctg | ctc | gct | ggg | gcc | gcc | tgg | gcg | ccc | ccg | cct | aac | ctc | ccg | gac | 96 |
| Leu | Leu | Leu | Ala | Gly | Ala | Ala | Trp | Ala | Pro | Pro | Pro | Asn | Leu | Pro | Asp | |
| | | | | 20 | | | | | 25 | | | | | 30 | | |
| ccc | aag | ttc | gag | agc | aaa | gcg | gcc | ttg | ctg | gcg | gcc | cgg | ggg | ccc | gaa | 144 |
| Pro | Lys | Phe | Glu | Ser | Lys | Ala | Ala | Leu | Leu | Ala | Ala | Arg | Gly | Pro | Glu | |
| | | | | 35 | | | | | 40 | | | | | 45 | | |
| gag | ctt | ctg | tgc | ttc | acc | gag | cgg | ttg | gag | gac | ttg | gtg | tgt | ttc | tgg | 192 |
| Glu | Leu | Leu | Cys | Phe | Thr | Glu | Arg | Leu | Glu | Asp | Leu | Val | Cys | Phe | Trp | |
| | 50 | | | | | 55 | | | | | 60 | | | | | |
| gag | gaa | gcg | gcg | agc | gct | ggg | gtg | ggc | ccg | ggc | aac | tac | agc | ttc | tcc | 240 |
| Glu | Glu | Ala | Ala | Ser | Ala | Gly | Val | Gly | Pro | Gly | Asn | Tyr | Ser | Phe | Ser | |
| 65 | | | | | 70 | | | | | 75 | | | | | 80 | |
| tac | cag | ctc | gag | gat | gag | cca | tgg | aag | ctg | tgt | cgc | ctg | cac | cag | gct | 288 |
| Tyr | Gln | Leu | Glu | Asp | Glu | Pro | Trp | Lys | Leu | Cys | Arg | Leu | His | Gln | Ala | |
| | | | | 85 | | | | | 90 | | | | | 95 | | |
| ccc | acg | gct | cgt | ggt | gcc | gta | cgc | ttc | tgg | tgt | tcg | ctg | cct | aca | gcc | 336 |
| Pro | Thr | Ala | Arg | Gly | Ala | Val | Arg | Phe | Trp | Cys | Ser | Leu | Pro | Thr | Ala | |
| | | | | 100 | | | | | 105 | | | | | 110 | | |
| gac | acg | tcg | agc | ttc | gtg | ccc | cta | gag | ttg | cgc | gtc | aca | gca | gcc | tcc | 384 |
| Asp | Thr | Ser | Ser | Phe | Val | Pro | Leu | Glu | Leu | Arg | Val | Thr | Ala | Ala | Ser | |
| | | | | 115 | | | | | 120 | | | | | 125 | | |
| ggc | gct | ccg | cga | tat | cac | cgt | gtc | atc | cac | atc | aat | gaa | gta | gtg | ctc | 432 |
| Gly | Ala | Pro | Arg | Tyr | His | Arg | Val | Ile | His | Ile | Asn | Glu | Val | Val | Leu | |
| | 130 | | | | | 135 | | | | | 140 | | | | | |
| cta | gac | gcc | ccc | gtg | ggg | ctg | gtg | gcg | cgg | ttg | gct | gac | gag | agc | ggc | 480 |
| Leu | Asp | Ala | Pro | Val | Gly | Leu | Val | Ala | Arg | Leu | Ala | Asp | Glu | Ser | Gly | |
| 145 | | | | | 150 | | | | | 155 | | | | | 160 | |
| cac | gta | gtg | ttg | cgc | tgg | ctc | ccg | ccg | cct | gag | aca | ccc | atg | acg | tct | 528 |
| His | Val | Val | Leu | Arg | Trp | Leu | Pro | Pro | Pro | Glu | Thr | Pro | Met | Thr | Ser | |
| | | | | 165 | | | | | 170 | | | | | 175 | | |
| cac | atc | cgc | tac | gag | gtg | gac | gtc | tcg | gcc | ggc | aac | ggc | gca | ggg | agc | 576 |
| His | Ile | Arg | Tyr | Glu | Val | Asp | Val | Ser | Ala | Gly | Asn | Gly | Ala | Gly | Ser | |
| | | | | 180 | | | | | 185 | | | | | 190 | | |
| gta | cag | agg | gtg | gag | atc | ctg | gag | ggc | cgc | acc | gag | tgt | gtg | ctg | agc | 624 |
| Val | Gln | Arg | Val | Glu | Ile | Leu | Glu | Gly | Arg | Thr | Glu | Cys | Val | Leu | Ser | |
| | 195 | | | | | 200 | | | | | 205 | | | | | |
| aac | ctg | cgg | ggc | cgg | acg | cgc | tac | acc | ttc | gcc | gtc | cgc | gcg | cgt | atg | 672 |
| Asn | Leu | Arg | Gly | Arg | Thr | Arg | Tyr | Thr | Phe | Ala | Val | Arg | Ala | Arg | Met | |
| | 210 | | | | | 215 | | | | | 220 | | | | | |
| gct | gag | ccg | agc | ttc | ggc | ggc | ttc | tgg | agc | gcc | tgg | tcg | gag | cct | gtg | 720 |
| Ala | Glu | Pro | Ser | Phe | Gly | Gly | Phe | Trp | Ser | Ala | Trp | Ser | Glu | Pro | Val | |
| 225 | | | | | 230 | | | | | 235 | | | | | 240 | |
| tcg | ctg | ctg | acg | cct | agc | gac | ctg | gac | ccc | ctc | atc | ctg | acg | ctc | tcc | 768 |
| Ser | Leu | Leu | Thr | Pro | Ser | Asp | Leu | Asp | Pro | Leu | Ile | Leu | Thr | Leu | Ser | |
| | | | | 245 | | | | | 250 | | | | | 255 | | |
| ctc | atc | ctc | gtg | gtc | atc | ctg | gtg | ctg | acc | gtg | ctc | gcg | ctg | ctc | | 816 |
| Leu | Ile | Leu | Val | Val | Ile | Leu | Val | Leu | Thr | Val | Leu | Ala | Leu | Leu | | |
| | | | | 260 | | | | | 265 | | | | | 270 | | |

```
tcc cac cgc cgg gct ctg aag cag aag atc tgg cct ggc atc ccg agc      864
Ser His Arg Arg Ala Leu Lys Gln Lys Ile Trp Pro Gly Ile Pro Ser
        275                 280                 285 cca gag agc gag ttt gaa ggc ctc ttc acc acc cac aag ggt aac ttc      912
Pro Glu Ser Glu Phe Glu Gly Leu Phe Thr Thr His Lys Gly Asn Phe
    290                 295                 300 cag ctg tgg ctg tac cag aat gat ggc tgc ctg tgg tgg agc ccc tgc      960
Gln Leu Trp Leu Tyr Gln Asn Asp Gly Cys Leu Trp Trp Ser Pro Cys
305                 310                 315                 320 acc ccc ttc acg gag gac cca cct gct tcc ctg gaa gtc ctc tca gag     1008
Thr Pro Phe Thr Glu Asp Pro Pro Ala Ser Leu Glu Val Leu Ser Glu
                325                 330                 335 cgc tgc tgg ggg acg atg cag gca gtg gag ccg ggg aca gat gat gag     1056
Arg Cys Trp Gly Thr Met Gln Ala Val Glu Pro Gly Thr Asp Asp Glu
            340                 345                 350 ggc ccc ctg ctg gag cca gtg ggc agt gag cat gcc cag gat acc tat     1104
Gly Pro Leu Leu Glu Pro Val Gly Ser Glu His Ala Gln Asp Thr Tyr
        355                 360                 365 ctg gtg ctg gac aaa tgg ttg ctg ccc cgg aac ccg ccc agt gag gac     1152
Leu Val Leu Asp Lys Trp Leu Leu Pro Arg Asn Pro Pro Ser Glu Asp
370                 375                 380 ctc cca ggg cct ggt ggc agt gtg gac ata gtg gcc atg gat gaa ggc     1200
Leu Pro Gly Pro Gly Gly Ser Val Asp Ile Val Ala Met Asp Glu Gly
385                 390                 395                 400 tca gaa gca tcc tcc tgc tca tct gct ttg gcc tcg aag ccc agc cca     1248
Ser Glu Ala Ser Ser Cys Ser Ser Ala Leu Ala Ser Lys Pro Ser Pro
                405                 410                 415 gag gga gcc tct gct gcc agc ttt gag tac act atc ctg gac ccc agc     1296
Glu Gly Ala Ser Ala Ala Ser Phe Glu Tyr Thr Ile Leu Asp Pro Ser
            420                 425                 430 tcc cag ctc ttg cgt cca tag                                         1317
Ser Gln Leu Leu Arg Pro
        435
```

<210> SEQ ID NO 5
<211> LENGTH: 438
<212> TYPE: PRT
<213> ORGANISM: Homo sapiens

<400> SEQUENCE: 5

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
                20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140
```

```
Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro
        435
```

<210> SEQ ID NO 6
<211> LENGTH: 1317
<212> TYPE: DNA
<213> ORGANISM: Homo sapiens
<220> FEATURE:
<221> NAME/KEY: CDS
<222> LOCATION: (1)..(1317)
<223> OTHER INFORMATION:
<221> NAME/KEY: terminator
<222> LOCATION: (1315)..(1317)
<223> OTHER INFORMATION:

<400> SEQUENCE: 6

```
atg gac cac ctc ggg gcg tcc ctc tgg ccc cag gtc ggc tcc ctt tgt      48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac      96
Leu Leu Leu Ala Gly Ala Ala Trp Ala Pro Pro Pro Asn Leu Pro Asp
            20                  25                  30
```

```
ccc aag ttc gag agc aaa gcg gcc ttg ctg gcg gcc cgg ggg ccc gaa      144
Pro Lys Phe Glu Ser Lys Ala Ala Leu Leu Ala Ala Arg Gly Pro Glu
         35                  40                  45 gag ctt ctg tgc ttc acc gag cgg ttg gag gac ttg gtg tgt ttc tgg      192
Glu Leu Leu Cys Phe Thr Glu Arg Leu Glu Asp Leu Val Cys Phe Trp
 50                  55                  60 gag gaa gcg gcg agc gct ggg gtg ggc ccg ggc aac tac agc ttc tcc      240
Glu Glu Ala Ala Ser Ala Gly Val Gly Pro Gly Asn Tyr Ser Phe Ser
 65                  70                  75                  80 tac cag ctc gag gat gag cca tgg aag ctg tgt cgc ctg cac cag gct      288
Tyr Gln Leu Glu Asp Glu Pro Trp Lys Leu Cys Arg Leu His Gln Ala
                 85                  90                  95 ccc acg gct cgt ggt gcc gta cgc ttc tgg tgt tcg ctg cct aca gcc      336
Pro Thr Ala Arg Gly Ala Val Arg Phe Trp Cys Ser Leu Pro Thr Ala
        100                 105                 110 gac acg tcg agc ttc gtg ccc cta gag ttg cgc gtc aca gca gcc tcc      384
Asp Thr Ser Ser Phe Val Pro Leu Glu Leu Arg Val Thr Ala Ala Ser
            115                 120                 125 ggc gct ccg cga tat cac cgt gtc atc cac atc aat gaa gta gtg ctc      432
Gly Ala Pro Arg Tyr His Arg Val Ile His Ile Asn Glu Val Val Leu
130                 135                 140 cta gac gcc ccc gtg ggg ctg gtg gca tgc ttg gct gac gag agc ggc      480
Leu Asp Ala Pro Val Gly Leu Val Ala Cys Leu Ala Asp Glu Ser Gly
145                 150                 155                 160 cac gta gtg ttg cgc tgg ctc ccg ccg cct gag aca ccc atg acg tct      528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc      576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc      624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg      672
Asn Leu Arg Gly Arg Thr Arg Tyr Thr Phe Ala Val Arg Ala Arg Met
    210                 215                 220 gct gag ccg agc ttc ggc ggc ttc tgg agc gcc tgg tcg gag cct gtg      720
Ala Glu Pro Ser Phe Gly Gly Phe Trp Ser Ala Trp Ser Glu Pro Val
225                 230                 235                 240 tcg ctg ctg acg cct agc gac ctg gac ccc ctc atc ctg acg ctc tcc      768
Ser Leu Leu Thr Pro Ser Asp Leu Asp Pro Leu Ile Leu Thr Leu Ser
                245                 250                 255 ctc atc ctc gtg gtc atc ctg gtg ctg ctg acc gtc ctc gcg ctg ctc      816
Leu Ile Leu Val Val Ile Leu Val Leu Leu Thr Val Leu Ala Leu Leu
            260                 265                 270 tcc cac cgc cgg gct ctg aag cag aag atc tgg cct ggc atc ccg agc      864
Ser His Arg Arg Ala Leu Lys Gln Lys Ile Trp Pro Gly Ile Pro Ser
        275                 280                 285 cca gag agc gag ttt gaa ggc ctc ttc acc acc cac aag ggt aac ttc      912
Pro Glu Ser Glu Phe Glu Gly Leu Phe Thr Thr His Lys Gly Asn Phe
    290                 295                 300 cag ctg tgg ctg tac cag aat gat ggc tgc ctg tgg tgg agc ccc tgc      960
Gln Leu Trp Leu Tyr Gln Asn Asp Gly Cys Leu Trp Trp Ser Pro Cys
305                 310                 315                 320 acc ccc ttc acg gag gac cca cct gct tcc ctg gaa gtc ctc tca gag     1008
Thr Pro Phe Thr Glu Asp Pro Pro Ala Ser Leu Glu Val Leu Ser Glu
                325                 330                 335 cgc tgc tgg ggg acg atg cag gca gtg gag ccg ggg aca gat gat gag     1056
Arg Cys Trp Gly Thr Met Gln Ala Val Glu Pro Gly Thr Asp Asp Glu
            340                 345                 350
```

```
ggc ccc ctg ctg gag cca gtg ggc agt gag cat gcc cag gat acc tat       1104
Gly Pro Leu Leu Glu Pro Val Gly Ser Glu His Ala Gln Asp Thr Tyr
            355                 360                 365 ctg gtg ctg gac aaa tgg ttg ctg ccc cgg aac ccg ccc agt gag gac       1152
Leu Val Leu Asp Lys Trp Leu Leu Pro Arg Asn Pro Pro Ser Glu Asp
370                 375                 380 ctc cca ggg cct ggt ggc agt gtg gac ata gtg gcc atg gat gaa ggc       1200
Leu Pro Gly Pro Gly Gly Ser Val Asp Ile Val Ala Met Asp Glu Gly
385                 390                 395                 400 tca gaa gca tcc tcc tgc tca tct gct ttg gcc tcg aag ccc agc cca       1248
Ser Glu Ala Ser Ser Cys Ser Ser Ala Leu Ala Ser Lys Pro Ser Pro
            405                 410                 415 gag gga gcc tct gct gcc agc ttt gag tac act atc ctg gac ccc agc       1296
Glu Gly Ala Ser Ala Ala Ser Phe Glu Tyr Thr Ile Leu Asp Pro Ser
            420                 425                 430 tcc cag ctc ttg cgt cca tag                                            1317
Ser Gln Leu Leu Arg Pro
            435

<210> SEQ ID NO 7
<211> LENGTH: 438
<212> TYPE: PRT
<213> ORGANISM: Homo sapiens

<400> SEQUENCE: 7

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Cys Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255
```

```
Leu Ile Leu Val Val Ile Leu Val Leu Leu Thr Val Leu Ala Leu Leu
                260                 265                 270

Ser His Arg Arg Ala Leu Lys Gln Lys Ile Trp Pro Gly Ile Pro Ser
            275                 280                 285

Pro Glu Ser Glu Phe Glu Gly Leu Phe Thr Thr His Lys Gly Asn Phe
        290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ser Phe Glu Tyr Thr Ile Leu Asp Pro Ser
            420                 425                 430

Ser Gln Leu Leu Arg Pro
        435

<210> SEQ ID NO 8
<211> LENGTH: 28
<212> TYPE: DNA
<213> ORGANISM: Homo sapiens

<400> SEQUENCE: 8
ctcgtcagcc aagcatgcca ccagcccc                                          28

<210> SEQ ID NO 9
<211> LENGTH: 13
<212> TYPE: PRT
<213> ORGANISM: Homo sapiens

<400> SEQUENCE: 9

Pro Val Gly Leu Val Ala Arg Leu Ala Asp Glu Ser Gly
1               5                   10

<210> SEQ ID NO 10
<211> LENGTH: 13
<212> TYPE: PRT
<213> ORGANISM: Murine

<400> SEQUENCE: 10

Pro Ala Gly Leu Leu Ala Arg Arg Ala Glu Glu Gly Ser
1               5                   10

<210> SEQ ID NO 11
<211> LENGTH: 13
<212> TYPE: PRT
<213> ORGANISM: Rattus norvegicus

<400> SEQUENCE: 11

Pro Ala Gly Leu Leu Ala Arg Arg Ala Glu Glu Gly Ser
1               5                   10
```

EFFICIENT CULTURE OF STEM CELLS FOR THE PRODUCTION OF HEMOGLOBIN

BACKGROUND OF THE INVENTION

Erythropoiesis

Erythropoiesis is the production of red blood cells. Under normal physiological conditions, erythropoiesis is principally regulated by erythropoietin (Epo), a hormone produced by the kidney in response to hypoxia. Erythropoietin, produced by the renal peritubular endothelium, circulates to the bone marrow where it stimulates committed stem cell progeny called erythroid progenitors to produce red blood cells.

Two distinct types of erythroid progenitors have been identified based on their abilities to form morphologically recognizable colonies when grown in semi-solid media such as methylcellulose. The burst forming unit-erythroid (BFU-E) represents the earliest identifiable progenitor fully committed to erythropoiesis. The BFU-E forms large multi-lobular hemoglobinized colonies, possesses a capacity for self-renewal and most (80–90%) are quiescent. BFU-E differentiate to give rise to the colony forming unit-erythroid (CFU-E). The CFU-E is a more differentiated erythroid progenitor which forms smaller hemoglobinized colonies and lacks the capacity of self-renewal. The majority of CFU-E are actively dividing. As BFU-E differentiate into CFU-E there is a loss in the expression of the primitive stem cell surface glycoprotein CD34, and an increase in the expression of the erythropoietin receptor (EpoR) and the transferrin receptor (CD71). Although BFU-E express low numbers of receptors for erythropoietin, they are stimulated by Epo to proliferate and differentiate into CFU-E which, in turn, express higher levels of the Epo receptors.

Erythroid Cell Proliferation and Differentiation

Erythroid proliferation and the differentiation beyond the CFU-E stage is dependent upon erythropoietin and is characterized by the expression of the red blood cell membrane protein glycophorin A, the accumulation of additional erythroid-specific membrane proteins, and the induction of hemoglobin synthesis. The later stages of erythroid differentiation are best characterized by the accumulation of hemoglobin, which accounts for approximately 95% of the protein present in the mature red call. Erythropoietin-stimulated hemoglobin synthesis is normally coordinated within differentiating red cell precursors so that the synthesis of the constituent alpha and beta globin chains is concurrent with the synthesis of heme.

Globin genes, as well as other genes encoding multiple enzymes along the heme synthesis pathway are transactivated by the major erythroid transcription factor, GATA-1, which is expressed following the activation of the Epo receptor by the binding of Epo. Whether Epo will support primarily erythroid differentiation or proliferation appears to depend on the concentration of Epo and the status of the cell cycle. Low concentrations of Epo support β-globin production and prolong the G1 phase of the cell cycle, whereas higher Epo concentrations promote cell proliferation and shorten the G1 phase.

Erythropoietin Receptor

Erythropoietin stimulates erythroid proliferation and differentiation by interacting with a specific receptor expressed almost exclusively on erythroid progenitors. The murine and human EpoR genes and cDNAs have been cloned (D'Andrea et al. (1989) Cell 57:277, Winkelmann et al (1990) Blood 76:24, Jones et al (1990) Blood 76:31). Sequence analysis of the isolates cDNAs revealed that the murine and human EpoRs are 507 and 508 amino acids long respectively, sharing an overall 82% amino acid identity. The topology of the EpoR is such that there is an amino terminal extracellular domain consisting of 226 amino acid (after cleavage of the 24 amino acid signal peptide), a 22 amino acid transmembrane domain and a 236 amino acid intracellular domain. The EpoR is a member of the cytokine receptor superfamily and possesses the characteristic pentapeptide WSXWS motif along with four conserved cysteine residues within the extracellular domain.

The binding of erythropoietin to the EpoR results in the phosphorylation of the intracellular tyrosine kinase, JAK2, which, in turn, phosphorylates several intracellular proteins including STAT5, PI3 kinase and vav. Evidence suggests that activation of second messengers by phosphorylation contributes to the Epo-induced proliferative response; however, the molecular basis which determines whether an erythroid cell will either proliferate or differentiate in response to Epo is unknown.

Characterization of EpoR Mutations

Various mutations have been described which render the murine EpoR either hypersensitive to Epo or constitutively active. Most studies into the functionality of the mutated EpoRs have been conducted using the BaF3 cell line. BaF3 cells are a murine IL-3-dependent pre-B cell line. These cells can be rendered IL-3-independent by over-expressing the EpoR and supplanting murine IL-3("mIL-3") with human Epo. Using this model, a frame-shift mutation resulting in the replacement of the C-terminal 42 amino acids of EpoR with Ala-Leu was shown to render the murine EpoR hypersensitive (Yoshimura et al (1990) Nature 348:647). This truncated EpoR, when expressed in BaF3 cells, is 3–5 times more responsive to Epo than the wild-type EpoR. It has been demonstrated that this C-terminal truncation removes a negative regulatory domain from the intracellular domain of the EpoR (Klingmuller et al (1995) Cell 80:729–738, D'Andrea (1991) Mol Cel Biol 11:1980). Normally, the hematopoietic protein tyrosine phosphatase SH-PTP1 docks to the C-terminal, dephosphorylating and inactivating JAK2 and thereby decreasing the signalling of the activated EpoR. Removal of this C-terminal negative regulatory domain prevents SH-PTP1 from binding to the EpoR thus resulting in prolonged signalling due to the delayed inactivation of JAK2. Transgenic mice have been generated which express a C-terminal truncated hypersensitive EpoR under the control of the β-actin promoter (Kirby et al (1996) Proc Natl Acad Sci 93:9402). Phenotypically the trangenic mice were normal; however, upon treatment with exogenous Epo there was a marked increase in pluripotent, clonogenic hematopoietic cells (CFU-S) in the transgenic mice as compared to the normal controls. CFU-S are pluripotent hematopoietic progenitors which give rise to granulocytes, erythroid cells, macrophage and megakaryocytes. The number of committed erythroid progenitors (BFU-E and CFU-E) were not significantly different between the transgenic and control mice.

A constitutively active form of the murine EpoR (but not the human EpoR) has also been previously identified. A point mutation whereby Arg129 (position is relative to the putative amino terminus at residue 25), which resides within the extracellular domain of the murine EpoR, is replaced with a Cys moiety (EpoR(R129C)) rendering this receptor constitutively active. Over-expression of EpoR(R129C) permits cytokine-independent growth of BaF3 cells and renders these cells tumourigenic in nude mice (Yoshimura et al (1990) Nature 348:647). Mechanistically it is thought that the R129C mutation within the murine EpoR renders it constitutively active by allowing the receptors to dimerize.

Similarly, mutation of either Glu132 or Glu133 (position is relative to the putative amino terminus at residue 25) to a Cys residue within the extracellular domain of the murine EpoR also results in a constitutively active EpoR (Watowich et al (1994) Mol Cell Biol 14:3535). A truncated murine EpoR containing an R129C mutation has also been identified and is constitutively active (Yoshimura et al (1990) Nature 348:647).

In vivo studies whereby the env gene of the spleen focus-forming virus is replaced by EpoR(R129C) have demonstrated that the modified virus induces transient thrombocytosis and erythrocytosis in infected mice and that the EpoR(R129C) stimulates the proliferation of committed megakaryocytic and erythroid progenitors as well as non-erythroid multipotent progenitors (Longmore et al (1994) Mol Cell Biol 14:2266–2277). Eight different multiphenotypic immortal cell lines, including primitive erythroid, lymphoid and monocytic cells, were isolated from the infected mice. All of these lines contained a mutant form of the p53 gene. These data suggest that a constitutively active form of the murine EpoR can induce proliferation and lead to transformation of nonerythroid as well as very immature erythroid progenitor cells when accompanied by a mutation of the p53 gene. A constitutively active form of the murine EpoR has been transfected into fetal liver cells (Pharr et al (1993) Proc Natl Acad Sci 90:938) and into pluripotent progenitors cells (Pharr et al (1994) Proc Natl Acad Sci 91:7482). When transfected into fetal liver cells, the activated EpoR eliminated the Epo requirement of CFU-E to form erythrocytes after 2–5 days in culture; however, this receptor did not support BFU-E development in the absence of Epo. The effect of Epo on the development of BFU-E was not investigated. Introduction of this constitutively active murine EpoR into pluripotent progenitors supported erythroid development in mixed colonies (GEMM) in the absence of Epo; however, its effect on committed erythroid progenitors (BFU-E or CFU-E) was not reported. Expression of this receptor did not alter the developmental potential of the infected pluripotent progenitors.

Several mutations within the intracellular domain of the human EpoR have been described for patients with primary familial and congenital polycythemia (PFCP). This disorder is characterized by elevated red blood cell mass and low serum Epo levels. Six of eight mutations result in truncation of the EpoR rendering them hypersensitive to Epo (Kralovics et al (1997) Blood 90:2057–2061). A constitutively active form of the human EpoR has not been described to date.

In Vitro Erythroid Cell Expansion and Differentiation

Traditionally, media for mammalian cell culture included a certain percentage of fetal bovine serum (FBS). However, serum contains undefined components, which may vary from batch to batch and may also be a source of contamination and growth factors. These materials may complicate the identification of multiple interactions that control proliferation and differentiation. To address these issues, a variety of serum-free fully defined media for the culture of hematopoietic cells has been described. Many of these formulations are similar in that they all include a basal medium such as IMDM, albumin, hormones and a source of fatty acids such as lipids and low density lipoproteins. As early as 1980, Iscove et al (Exp. Cell Res. 126:121–126) reported the complete replacement of serum with albumin, transferrin, iron, unsaturated fatty acids, lecithin and cholesterol in cultures of primary erythroid precursors. Recently, Polini et al (1997, Hematol. Cell Ther. 39:49–58) used a serum-free medium consisting of IMDM supplemented with BSA, human transferrin and insulin, soybean lecithin, cholesterol, hydrocortisone, inositol, folic acid and α-thioglycerol to maintain human hematopoietic stem cells for an extended period of time ex vivo.

Several serum-free media have also been described for the ex vivo expansion and differentiation of erythrocytes from hematopoietic stem cells. Previously, Fibach et al (1991, Intl. J. Cell Cloning 9:57–64) described a two-stage culture method for the generation of erythrocytes from whole blood LDMNC. In the first stage, cells were cultured in the presence of FBS, "5637 conditioned medium" and cyclosporin A and in the second stage, cells were cultured in the presence of Epo and FBS at reduced $O_2$ tensions. While this method yielded more normoblasts/erythocytes than were contained in BFU-E colonies seeded in methylcellulose on day one, it employed both FBS and a conditioned medium. Both these components contain unknown substances which may be potential sources of contamination making this method undesirable.

Lansdorp and Dragowska (1992, J. Exp. Med. 175:1501–1509) and Malik et al (1998, Blood 91:2664–2671) reported the generation of erythrocytes from $CD34^+$cells in serum-free medium. In both cases, $CD34^+$ cells were seeded in serum-free medium and serially passaged for the duration of the culture. Cells were reported to progress through erythropoiesis with the majority of the cells acquiring erythroid markers such as glycophorin A (GlyA) and the morphology of erythroblasts. With the addition of 2% BSA, 10 ug/ml insulin, 200 ug/ml transferrin, 40 ug/ml LDL and 20 ng/ml IL-3, 50 ng/ml SCF, 3U/ml Epo and 10 ng/ml IL-6 to IMDM, Lansdorp and Dragowska obtained $10^5$ and $10^6$ fold expansion from two samples of $CD34^+$cells. The serum free formulation of Malik et al was composed of IMDM with 1% BSA, $10^{-6}$M hydrocortisone and 10 U/ml Epo, 1 pg/ml GM-CSF and 0.01 U/ml IL-3. Although the degree of expansion was not reported, at culture termination, 10% to 40% of the cells cultured in this medium were reported to be nearly fully differentiated reticulocytes.

SUMMARY OF INVENTION

This invention teaches a method for the large-scale serum-free expansion of primary erythroid cells from $CD34^+$cells. This method results in greater than 10,000,000-fold expansion of CD34+ cells of which more than 95% are erythroid in nature. Cells cultured according to the method of the invention, including erythroid progenitors, can be efficiently transfected by means of electroporation. Two constitutively active forms of the human EpoR and a hypersensitive form of the human EpoR are also described and their utility in prolonging the lifespan of erythroid progenitors in culture is demonstrated.

A truncated (t439)(relative to the imitation Met residue) version of the human EpoR gene has been constructed which contains a point mutation (R154C) (relative to the imitation Met residue). Transfection of this EpoR ("EpoR(t439; R154C) into a cytokine-dependent cell line supports cell population expansion in the absence of exogenous cytokines. Transfection of this construct into hematopoietic progenitor cells increases the expansion of BFU-E, as detected using colony-forming assays.

It is thus an object of the invention to provide a serum free defined medium substantially free of fatty acids and hydrocortisone comprising effective amounts of: serum albumin, insulin, transferrin, IL-3, SCF, and EPO.

It is a further object of the invention to provide a method of producing an expanded population of erythroid cells comprising culturing an initial population containing erythroid precursors in a serum free defined medium.

It is a further object of the invention to provide a method of producing a differentiated population of erythroid cells comprising culturing an initial population containing erythroid precursors in a serum free defined medium.

It is a further object of the invention to provide a method of producing a population of erythroid cells suitable for high efficiency non-viral transfection comprising culturing an initial population containing erythroid precursors in a serum free defined medium comprising serum albumin, insulin, transferrin, IL-3, SCF, and EPO.

It is a further object of the invention to provide a method of producing a population of erythroid cells suitable for high efficiency non-viral transfection comprising culturing an initial population containing erythroid precursors in a serum free defined medium comprising serum albumin, insulin, transferrin, IL-3, SCF, EPO, and a fatty acid source, and subsequently treating the cells for high efficiency non-viral transfection.

It is a further object of the invention to provide a method of producing a population of erythroid cells having a hemoglobin (Hb) content in excess of normal levels comprising culturing an initial population in a serum-free defined medium comprising serum albumin, insulin, transferrin, IL-3, SCF, and EPO and essentially free of fatty acid sources.

It is a further object of the invention to provide a population of erythroid cells suitable for high efficiency non-viral transfection.

It is a further object of the invention to provide a population of erythroid cells having a Hb content in excess of normal levels.

It is a further object of the invention to provide a method of transfecting erythroid cells by electroporation comprising:

(a) culturing an initial cell population in a serum free defined culture medium comprising effective amounts of serum albumin, insulin, transferrin, IL-3, SCF, Epo, and LDLs, and (b) electroporating cells in the presence of suitable DNA It is a further object of the invention to provide a constitutively active human EpoR.

It is a further object of the invention to provide a human EpoR truncated at amino acid 439.

It is a further object of the invention to provide a human EpoR having an R→C mutation at amino acid residue 154.

It is a further object of the invention to provide a human EpoR having an R→C mutation at amino acid residue 154 which is truncated at amino acid residue 439.

It is a further object of the invention to provide an erythroid cell expressing a human EpoR having an R→C mutation at amino acid residue 154 which is truncated at amino acid residue 439.

It is a further object of the invention to provide a use of an effective amount of a suitable heme synthesis inhibitor in enhancing the expansion of a population of erythroid cells.

It is a further object of the invention to provide a use of an expanded population of erythroid cells in hematologic support.

It is a further object of the invention to provide a use of a differentiated population of erythroid cells in hematologic support.

It is a further object of the invention to provide a use of a population of erythroid cells suitable for high efficiency non-viral transfection in gene therapy.

It is a further object of the invention to provide a use of an expanded population of erythroid cells in in vitro viral replication.

It is a further object of the invention to provide a use of a differentiated population of erythroid cells in in vitro viral replication.

It is a further object of the invention to provide a use of an expanded population of erythroid cells in replicating parvovirus B19 in vitro.

It is a further object of the invention to provide a use of a differentiated population of erythroid cells in replicating parvovirus B19 in vitro.

It is a further object of the invention to provide a use of a hemoglobin source in enhancing Hb production in a population of erythroid cells expanded in the presence of a heme synthesis inhibitor.

BRIEF DESCRIPTION OF THE DRAWINGS

FIG. 1 depicts results obtained in Example 1, namely, scattergrams obtained from the FACS analysis of cord blood low density mononuclear cells (LDMNC) before and after lineage depletion as described in Example 1. Cells were labeled with antibodies to CD34 (HPCA-2-FITC) and CD45 (GAP8.3-PE) and were analyzed on a Coulter Epics Elite FACScan using forward and side light scatter and fluorescence intensity.

FIG. 9A (SEQ.ID.NO.4) is a representation of the cDNA sequence of the EpoR(t439).

FIG. 9B (SEQ.ID.NO.5) is a representation of the amino acid sequence of the EpoR(t439).

FIG. 10A (SEQ.ID.NO.6) is a representation of the cDNA sequence of the EpoR(t439; R154C).

FIG. 10B (SEQ.ID.NO.7) is a representation of the amino acid sequence of the EpoR(t439; R154C).

DETAILED DESCRIPTION OF THE PREFERRED EMBODIMENTS

Figure 2:
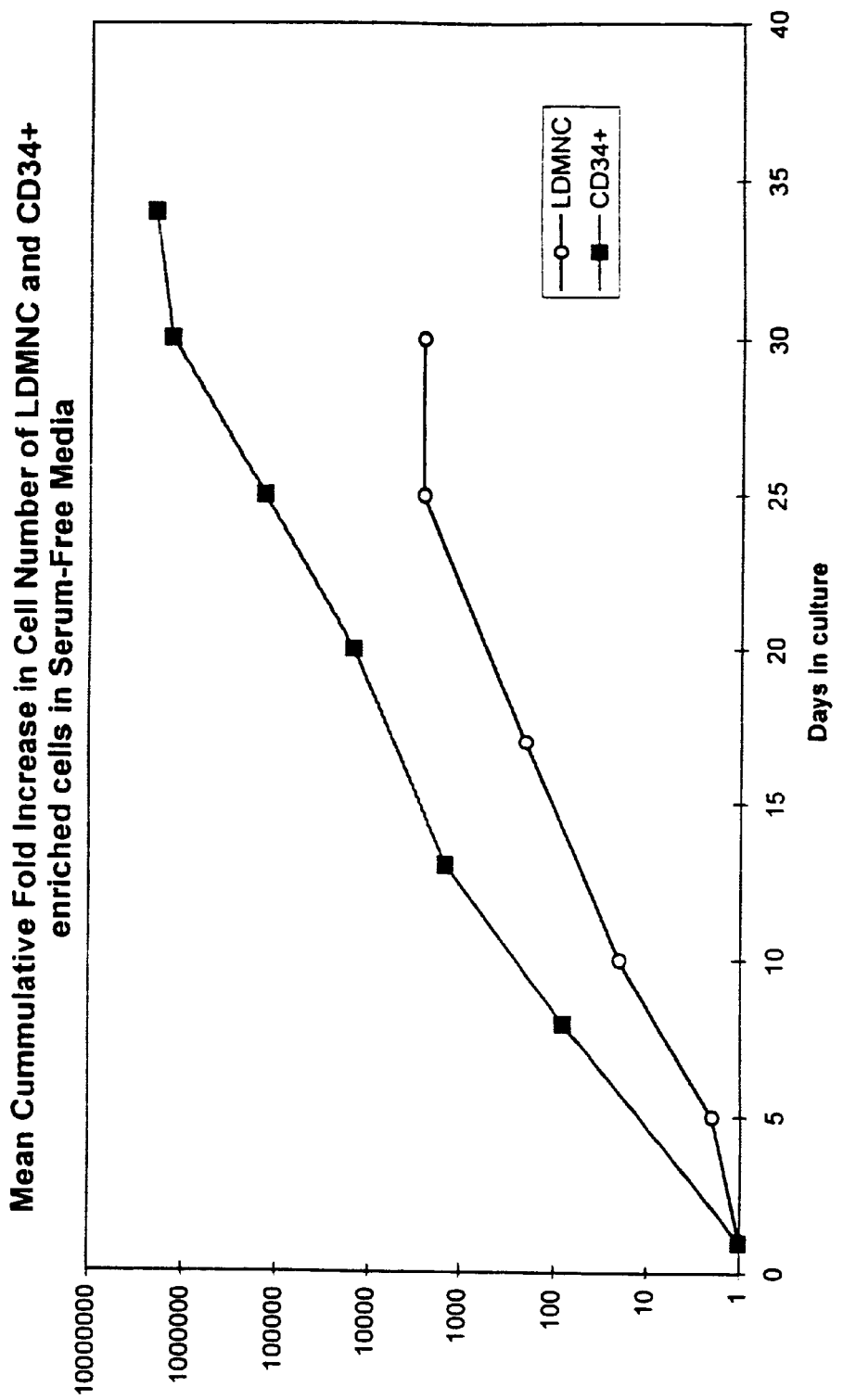
FIG. 2 is a graphical representation of cell population growth curves obtained in Example 1 describing the overall fold expansion of LDMNC over the duration of culture measured in days. The expansions of CD34$^+$enriched from umbilical cord blood (UCB) and unenriched LDMNC derived from the same source are represented. CD34$^+$ enriched cells were cultured in EPSFM+LDL as described in Example 1 and unenriched LDMNC were cultured in a comparable medium (X-Vivo™ with the addition of 5% umbilical cord blood plasma, 10 ng/ml IL-3, 50 ng/ml SCF and 2 U/ml EPO.

The present invention is directed to a serum free defined culture medium and methods of producing expanded and/or differentiated populations of erythroid cells suitable for high efficiency non-viral transfection. The invention is further directed to methods for the efficient non-viral transfection of cells and uses of cells produced by the methods of the invention. The invention is also directed to mutant EpoR's and uses of these mutant EpoRs.

The serum-free defined culture medium of the present invention allows the expansion and differentiation of erythroid cells from erythroid precursors within an initial population. The initial population may be derived from any cell population containing erythroid precursors, including umbilical cord blood, bone marrow, and peripheral blood. The initial cell population is preferably enriched for low density mononuclear cells (LDMNCs). As used herein, the phrase "erythroid cells" includes erythrocytes, BFU-E cells and CFU-E cells. As used herein, the term "erythroid precursors" means any cells capable of forming erythroid cells in vitro.

The serum free defined medium of the present invention preferably comprises serum albumin, insulin, transferrin, IL-3, stem cell factor ("SCF"), and Epo in effective amounts as its principle active components, and is essentially free of hydrocortisone and fatty acid sources such as LDLs. As used herein, the term "essentially free" means not containing enough to provide any measurable effect on the course of the process. In many instances, it will be desirable to supplement the serum-free defined medium of the present invention with low density lipoproteins (LDLs) or other sources of fatty acids, and/or heme synthesis inhibitors such as succinyl acetone acetone ("SA") and/or hemoglobin sources such as hemin. The components of the serum free defined medium may be obtained from a variety of suitable sources, as discussed below. In general, it is preferable to use components derived from the same species as the initial population, or having similar functional characteristics as components derived from that species. In some instances it will be desirable to use recombinantly produced components.

The serum albumin of the serum-free defined medium of the present invention may be obtained from any suitable source, including human or bovine serum albumin or from another immediate source, such as recombinant serum albumin, having functional charactoristics similar to bovine serum albumin. In some instances it will be desirable to obtain serum from the same source as the cell population to be expanded. Serum albumin concentrations in the serum-free defined medium of the present invention are from about 0.1 mg/ml to 15 mg/ml, preferably from about 0.75 mg/ml to 15 mg/ml, and even more preferably 10 mg/ml (1%).

The insulin in the serum-free defined medium of the present invention may be obtained from any suitable source, including human or bovine insulin, or insulin from another immediate source, such as recombinant insulin, having functional characteristics similar to human insulin. The concentration of insulin in the serum-free defined medium of the present invention is from about 0.1 to 100 $\mu$g/ml, preferably from about 1 to 50 $\mu$g/ml and even more preferably 10 $\mu$g/ml.

The transferrin in the serum-free defined medium of the present invention is preferably holo transferrin and may be obtained from any suitable source, including human or bovine transferrin, or transferrin from another immediate source, such as recombinant transferrin, having functional characteristics similar to those of human transferrin. The concentration of transferrin in the serum-free defined medium of the present invention is from about 1 to 500 $\mu$g/ml, preferably from about 50 to 250 $\mu$g/ml, and even more preferably 200 $\mu$g/ml.

The IL-3 in the serum-free defined medium of the present invention is preferably human IL-3, or IL-3 from another immediate source, such as recombinant human IL-3, having functional characteristics similar to human IL-3. The concentration of IL-3 in the serum-free defined medium of the present invention is from about 0.1 to 10 ng/ml, preferably from about 5 to 50 ng/ml and even more preferably 10 ng/ml.

The SCF in the serum-free defined medium of the present invention may be obtained from any suitable source, including human or murine SCF, or SCF from another immediate source, such as recombinant SCF, having functional characteristics similar to naturally produced human SCF. Where non-human derived SCF is used (for example murine SCF) in the culture of human cells it is desirable to use a higher concentration of SCF in the medium than would be necessary for human SCF. The concentration of human derived SCF in the serum-free defined medium of the present invention is from about 1 to 100 ng/ml, preferably from about 5 to 100 ng/ml and even more preferably 50 ng/ml.

The Epo in the serum-free defined medium of the present invention may be obtained from any suitable source, including human or murine Epo, or Epo from another immediate source, such as human recombinant Epo, having functional characteristics similar to naturally occurring human Epo. Where non-human derived Epo is employed in the culture of human cells, a higher concentration should be employed than would be necessary when using human Epo. The concentration of Epo in the serum-free defined medium of the present invention is from about 0.01 to 100 U/ml, preferably from about 0.1 to 10 U/ml and even more preferably 2 U/ml.

Where is desired to include a fatty acid source such as LDLs in the serum-free defined medium of the present invention this fatty acid source may be from any suitable source, including animal or plant fatty acids. The concentration of LDLs in the serum-free defined medium of the present invention is from about 1 to 100 $\mu$g/ml, preferably from about 5 and 50 $\mu$g/ml and even more preferably 40 $\mu$g/ml.

Where is desired to include SA in the serum-free defined medium of the present invention, the concentration of SA in the serum-free defined medium of the present invention is from about 10 to 500 µM, preferably from about 0.1 to 300 µM, more preferably from about 25 to 250 µM, and even more preferably 50 µM.

Where is desired to include hemin in the serum-free defined medium of the present invention this hemin may be obtained from any suitable source, including human or bovine hemin, or hemin from another immediate source, such as recombinant hemin, having functional charactoristics similar to those of human hemin. The concentration of hemin in the serum-free defined medium of the present invention is from about 10 to 500 µM, preferably from about 1 to 100 µM, more preferably from about 10 to 50 µM, and even more preferably 25 µM.

The ex vivo culture of hematopoietic stem and progenitor cells provides a means of characterizing the growth properties of stem and progenitor cells. In addition, large-scale expansion and differentiation of hematopoietic cells allows for the harvesting of erythroid-specific proteins for therapeutic and research use. The generation of large numbers (>10$^6$ cells) of terminally differentiated red blood cells from a limited number of hematopoietic stem cells will yield significant amounts of clinically relevant erythroid specific proteins such as hemoglobin. The in vitro production of large numbers or erythroid cells at various stages of differentiation will also provide cells suitable for gene transfer therapies and scientific experiments. Populations of expanded erythroid cells are also clinically valuable in the treatment of conditions including hemoglobinopathies and thalassemias. Expanded erythroid cells may be modified by known means such as gene transfer to produce stably transfected erythroid progenitors expressing one or more proteins of interest. Expanded cell populations can be produced which are suitable for use to provide hematologic support in instances where additional erythroid cells are needed, such as following marrow ablation wherein treatment with an expanded cell population can allow for the purging of tumor cells/expansion of non-malignant cells for autologous grafts and speed re-engraftment for allogeneic transplants. In addition, stem cell cultures may be used to generate an expanded target population in gene therapy protocols. Finally, certain viruses such as parvovirus B19 can only replicate in proliferating and differentiating erythroid cells. Thus, cells produced by the method of the present invention represent a useful vehicle for in vitro viral replication.

In order for cultured cells to be included in human therapeutic protocols, the reduction of potential sources of immunogenicity, which may result from the presence of non-human proteins, is desirable. Furthermore, it is important that potential sources of pathogenic contaminants such as viruses and mycoplasma be minimized. The serum-free defined culture medium described in the present invention is a medium the composition of which is designed to promote high levels of expansion and erythroid-specific differentiation of CD34$^+$cells, while minimizing potential sources of immunogenicity and pathogenic contaminants. Two specific embodiments of this medium, known as "EPSFM" and "EPSFM+LDL" are described in Table 1A and B.

TABLE 1A

Principle Active Ingredients of EPSFM

| Component | Concentration |
|---|---|
| IMDM | — |
| deionized BSA | 1% |
| bovine pancreatic insulin | 10 µg/ml |
| human transferrin (holo) | 200 µg/ml |
| rhIL-3 | 10 ng/ml |
| rhSCF | 50 ng/ml |
| rhEPO | 2 U/ml |

TABLE 1B

Principle Active Ingredients of EPSFM + LDL

| Component | Concentration |
|---|---|
| IMDM | — |
| deionized BSA | 1% |
| bovine pancreatic insulin | 10 µg/ml |
| human transferrin (holo) | 200 µg/ml |
| human LDL (low density lipoproteins) | 40 µg/ml |
| rhIL-3 | 10 ng/ml |
| rhSCF | 50 ng/ml |
| rhEPO | 2 U/ml |

SA is a potent inhibitor of δ-aminolevulonic acid dehydrogenase, the second enzyme in the heme synthesis pathway. SA has been shown to inhibit globin expression/hemoglobin production in a variety of erythroid differentiation models including DMSO-induced differentiation of MEL (Grandchamp B et al (1985) J Biol. Chem. 260:9630–5) and Friend leukemia cells (Battistini et al (1991) 78:2098–2103), sodium butyrate-induced differentiation of the K562 human erythroleukemia cell line (Kawasaki et al (1996) Arch Biochem Biophys 328:289–94), and Epo-dependent differentiation of primary human erythroid progenitors (Fibach et al (1995) Blood 85:2967–2974) and rat bone marrow cells (Beru et al (1983) J. Cell. Biochem. 21:93–105). SA has been shown to inhibit the growth of malignant murine erythroleukemic cells (Ebert et al (1981) Cancer Res 41:937–41) and induce apoptosis of primary human erythroid progenitors (Muta and Krantz (1995) J Cell Physiol. 163:38–50).

In light of the known inhibitory effects of SA, it was surprising that the inclusion of SA in the erythroid cell culture medium culture medium EPSFM+LDL significantly enhanced the expansion of CD34$^+$ cells ex vivo. This increase in cell expansion upon culture in EPSFM+LDL+SA was unexpected as SA has been shown to be toxic to erythroid colony-forming cells (Muta and Krantz (1995) J Cell Physiol. 163:38–50 and Mueller and Bell, U.S. patent application Ser. No. 08/917,913).

Suitable heme synthesis inhibitors may be used to enhance the expansion of erythroid cells. Suitable heme synthesis inhibitors are agents which, when used in an effective amount, enhance erythroid cell expansion to levels above those observed when comparable cells are cultured without the heme synthesis inhibitor but otherwise under substantially the same conditions. Suitable heme synthesis inhibitors can include SA, isonicotinic acid hydrazine and D,L-pencillamine. An effective amount of a heme synthesis inhibitor is an amount which allows enhanced erythroid cell expansion. Various heme synthesis inhibitors are known in the art and, in light of the present invention, it is within the capacity of a competent technician to identify suitable heme synthesis inhibitors and the effective amount of those heme synthesis inhibitors, without undue experimentation.

In a preferred use, a suitable heme synthesis inhibitor such as SA is added to the preferred erythroid cell culture medium EPSFM+LDL early (within the first 2 days after culture initiation) in culture and erythroid cells are expanded in the resultant medium. Alternately, a suitable heme synthesis inhibitor such as SA may be used in another suitable erythroid cell culture medium to enhance the expansion of erythroid cells. As used herein, the term "erythroid cell culture medium" means a culture medium suitable for use in expanding erythroid cells. Various erythroid cell culture media are known in the art (for example, Lansdorpe et al. (1992) *J. Exp. Med.* 175:1501, and Migliaccio (1992) *Blood* 79:2620), and it is within the capacity of a competent technician skilled in the art in light of the present invention to select, without undue experimentation, an appropriate erythroid cell culture medium and an appropriate concentration of SA to use to expand erythroid cells.

Heme sources such as hemin may be used in combination with heme synthesis inhibitors such as SA to enhance erythroid cell expansion and enhanced hemoglobin production in erythroid cells cultured in erythroid cell culture media, including EPSFM and EPSFM+LDL. As discussed herein, hemin may be added to erythroid cell culture media in addition to SA to enhance Hb production and to further enhance erythroid cell population expansion. SA may either be added early in culture at a similar time to the time of SA addition, or it may be added later in culture, preferably within 10 to 20 days after culture initiation.

Exogenous fatty acids or lipids, including cholesterol, free fatty acids, and phospholipids, have previously been found necessary for the expansion in culture of almost all cell types examined. (Sehmid (1991) *J. Biotech.* 17:155) Cells readily take up lipids and use them as a source of energy and as precursors for biosynthesis. Lipids typically added to serum-free media for hematopoietic cells include soybeans lethicin, cholesterol, oleic acids and low density lipoproteins (Lebkowsi et al (1995) Stem Cells 13:607–612).

Previously disclosed serum free media suitable for the expansion of erythroid cells almost all require the addition of exogenous sources of fatty acids. One group which reported a serum-free medium suitable for the expansion of erythroid cells without exogenous fatty acids was Malik et al. (*Blood* 91(8):2664, 1998). However, unlike the medium of the present invention, the medium of Malik et al. required the addition of the glucocorticoid hydrocortisone for effectiveness. It is frequently desirable to avoid the use of glucocorticoids, including hydrocortisone, in culture media due to the effects of these substances on cellular processes including suppressive effects on cells of the hematopoietic system and interference with normal insulin-mediated effects in erythroid cells.

Surprisingly, the serum-free defined culture medium of the present invention, as specifically embodied in EPSFM, supports significant expansion of erythroid cells in the absence of hydrocortisone and exogenous sources of fatty acids, such as LDL. Even more surprising, culture of cells in defined culture medium of the present invention (without LDLs) resulted in a large increase in hemoglobin (Hb) content per cell above the normal level observed in a typical EPSFM+LDL culture ("normal level" observed to be 8.8 pg/BZ+ cell in Example 3). In cells cultured in the defined medium of the present invention (without LDLs), hemoglobin content in excess of 20 pg/BZ+ cell were observed.

Erythroid cells cultured according to the method of the present invention are valuable as a means of replicating viruses in vitro. Methods of infecting cells with virus are well known in the art (for example see Munshie et al.(1993) 67(1):562). Suitable viruses for replication in erythroid cells cultured according to the method of the present invention are viruses which replicate in growing and differentiating erythroid cells. It is possible to identify suitable viruses with reference to the prior art. It is therefore well within the capability of a competent technician, in light of the present invention, to replicate suitable viruses in vitro, including parvovirus B19, using the cell expansion and differentiation method of the invention by infecting erythroid cells cultured according to the cell expansion and differentiation method of the invention with a suitable virus, such as parvovirus B19.

Gene Transfer

The expansion of hematopoietic cells in defined culture medium as described in the present invention can also provide target cells for gene therapy protocols. Gene therapy, or the transfer of exogenous DNA into human cells, can be used to correct or ameliorate a variety of clinical conditions. Although originally developed for the treatment of inherited diseases including those of improper globin expression, certain enzyme deficiencies and auto-immune disorders, gene therapy now encompasses a wide variety of potential uses including in the treatment of infectious disease such as HIV and in cancer therapy. For example, cells produced by the method of the invention can be transfected with transcribable genetic material encoding one or more protein products important to health or survival. Alternately or additionally, cells produced by the method of the invention can be transfected with transcribable genetic material encoding an anti-sense RNA capable of inhibiting the expression of an undesirable product which would otherwise be produced. Transfected cells may be infused into suitable subjects to treat or alleviate the symptoms of a pathological condition. The cells subjected to transfection may be derived from a cell population obtained from the patient who will be infused with the transfected cells. Alternatively, the cells to be transfected may be derived from a cell population obtained from a suitable MHC-compatible donor. In addition to gene therapy protocols, gene transfer into erythroid cells may be used to introduce genes coding for transcription or other factors to increase the production of hemoglobin or other erythroid-specific proteins. Gene transfer may also be used to introduce genes for growth factor receptors that have been mutated to render them either hypersensitive or constitutively active in order to reduce or alleviate the need for growth factors. Further, gene transfer can be used to introduce genes coding for proteins capable of immortalizing erythroid cells thus creating permanent cell lines.

The present invention provides a means for expressing foreign source DNA in cells and producing foreign source protein "Foreign Source DNA" as used herein refers to expressible DNA which is introduced into cells. Foreign source DNA may have a genetic sequence identical to DNA occurring naturally in the cell to be transfected. Alternatively, foreign source DNA may differ/source from DNA occurring naturally in the cell. Foreign source protein is protein encoded by foreign source DNA foreign source protein produced in the cell may be used to induce, modulate, or modify cellular processes such as gene expression. Alternatively, foreign source protein may be used to provide a source of a desired protein for use in other systems. For example, foreign source DNA encoding globin chains may be introduced into cells to produce foreign source protein, namely globin chains. These globin chains may then be purified for use in therapeutic and cell culture applications.

Once cells have been transfected with foreign source DNA, the cells may be screened by methods known in the art for the expression of the corresponding foreign source protein. Cells expressing the foreign source protein may then be cultured by standard means.

Foreign source proteins of particular interest include globin proteins, transcription factors, immortalising proteins, and genetically altered growth factor receptors.

The cDNA and amino acid sequence of various globin genes are known in the art and in light of the present invention it is within the capacity of a competent technician to produce such proteins in erythroid cells.

Transcription factors of particular interest include those which can be used to induce erythroid cell expansion and/or differentiation, such as: c-myb, v-ski, sci, gata-1 and pa-1-. The cDNA sequences of numerous transcription factors are known in the art and it is within the capacity of a competent technician in light of the present invention to produce transcription factors for foreign source DNA in erythroid cells.

Immortalising proteins which, when expressed in primary cell lines, allow the delay or prevent the senescence typically associated with long-term culture of such cell lines. Immortalising proteins of particular interest include: SV40 large T antigen, human papilloma virus proteins E6 and E7, c-myb, mutant p53, ras, myc, elc-1, hox11, polyoma middle T antigen, bel-Z, ans, qmv. The cDNA sequences of numerous immortalising proteins are known in the art. It is therefore within the capacity of a competent technician, in light of the present invention, to produce immortalising proteins in erythroid cells.

Genetically altered growth factor receptors may be produced as foreign source proteins in order to modulate or alter the growth factor requirements and/or responses of the transfected cells. Modified growth factor receptors of particular interest include constitutively active EpoRs such as those disclosed herein, as well as constitutively active SCF receptors such as that disclosed by Piaoetal (PNAS USA (1996)93(25):15665).

One particularly valuable embodiment of the present invention is an immortalised erythroid cell expressing high levels of globin genes. Such a cell may be produced by a competent technician in light of the present invention by transfecting a population of erythroid cells produced by the method of the invention with foreign source DNA encoding a suitable immortalising protein and foreign source DNA encoding suitable globin genes according to the method of the invention.

In light of the present invention it is within the capacity of a competent technician to determine what constitute suitable foreign source DNAs and suitable foreign source proteins. Thus, the present invention provides a method for recombinant protein expression wherein the recombinant protein is a foreign source protein. The present invention provides a method for the production of recombinant hemoglobin suitable for clinical and cell culture use.

The present invention provides a use for erythroid cells of the present invention in expressing immortalising protein.

Numerous genetic disorders are known which are amenable to treatment by gene therapy. For example, sickle cell anemia is a life-threatening disorder resulting from a well-characterized point mutation in the gene encoding the hemoglobin β chain, the normal sequence of which is known in the art. In light of the present invention, it is well within the capability of a competent technician to transfect a population of erythroid cells with transcribable genetic material encoding a desired gene product, such as a normal hemoglobin β-chain. These transfected cells can be infused into a suitable MHC compatible subject to allow the production of normal hemoglobin in the patient.

It will frequently be desirable to inhibit the production of mutant proteins in cells expressing mutant genes. This may be accomplished by transfecting cells with transcribable genetic material encoding an antisense RNA capable of inhibiting the translation of the mutant protein from its corresponding RNA. In the case of sickle cell anemia, in addition to transfecting cells with normal hemoglobin β-chain genes, it may also be desirable to inhibit the expression of the mutant hemoglobin β-chain gene in the transfected cell through the use of an anti-sense RNA specific to the mutant RNA. In light of the present invention, it is within the capacity of a competent technician to transfect a population of erythroid cells with transcribable genetic material encoding an antisense RNA of interest, such as an antisense RNA capable of inhibiting the translation of the mutant hemoglobin β-chain in cells from a subject with sickle-cell anemia.

Gene therapy of erythroid cells according to the method of the present invention is particularly well suited to the treatment or alleviation of the symptoms of conditions relating to mutations in genes expressed in erythroid cells. One example of such conditions are thalassemias resulting from mutations in one or more globin genes. Globin genes are well characterized, and many mutations resulting in thalassemia have been reported. It is therefore within the capacity of a competent technician, in light of the present invention, to identify subjects having thalassemias suitable for alleviation or treatment by gene therapy according to the present invention, and to alleviate or treat those thalassemia according to the method of the present invention.

A second example of conditions especially well suited for treatment by gene therapy using the method of the present invention are Epo-related conditions arising either from inadequate erythropoietin levels in the patient, or inadequate signalling by the EpoR upon Epo binding. Mutations in the EpoR have been identified which inhibit Epo binding to the EpoR or which inhibit normal EpoR signalling following Epo binding. The sequence of the human EpoR is known. It is therefore within the capacity of a competent technician, in light of the present invention, to identify subjects having Epo-related conditions suitable for alleviation of symptoms or treatment by gene therapy according to the present invention, and to alleviate the symptoms of, or treat, those Epo-related conditions according to the method of the present invention.

In particular, where a cause of a patient's Epo-related condition is known to be a mutation in the EpoR, that patient may be infused with suitable erythroid cells which have been transfected with and are expressing a gene encoding a functional EpoR. Additionally, it will sometimes be desirable to transfect erythroid cells with expressible genetic material encoding an anti-sense RNA which will inhibit the expression of the mutant EpoR, thereby reducing competition for Epo and/or dominant negative effects.

Where a cause of a patient's Epo-related condition is known to be insufficient Epo levels in the blood, it may be desirable to infuse the patient with erythroid cells produced according to the method of the invention which have been transfected with a suitable hypersensitive EpoR (such as EpoR(t439), a constitutively active EpoR (such as EpoR (R154C) or EpoR(t439,R154C)), or a normal EpoR under the control of a promoter which results in increased EpoR expression on the cell surface.

Electroporation

Electroporation is a means of gene transfer to mammalian cells which has many unique advantages over other commonly employed methods. In particular, electroporation does not require use of viral components or infectious agents and therefore the risk of contaminating helper viruses is reduced. In addition, electroporation can be applied to a wide variety of cell types, minimal manipulation of DNA is required and DNA is large as 150 kB can be transfected. Electroporation may be better suited to use in gene therapy than other non-viral methods of gene transfer because the exogenous DNA that enters a cell through the temporary pores created in the membrane may bypass the endosomal compartment.

Although electroporation has many advantages and has been used successfully to introduce DNA into hematopoietic cell lines, only low frequencies of transfection of primary hematopoietic cells such as expanded erythroid cell populations have been reported. (Toneguzzo and Keating (1986) Mol. Cell. Biol. 6;703–706, Narayanan et al (1989) Exp. Hematol. 17:832–835 and Takahashi et al (1992) Leuk. Res. 16:761–767). The present invention overcomes this limitation and describes a means of efficiently transfecting primary erythroid cells by electroporation.

The present invention provides a means for the efficient non-viral transfection of erythroid cells using electroporation. This is accomplished by: culturing an initial cell population in pre-electroporation medium prior to electroporation and electroporating the cells using standard means known in the art and discussed herein. Following electroporation, cells should be allowed to recover by placing the electroporated cells in a suitable post-electroporation medium. The pre-electroporation medium is a serum-free defined medium comprising effective amounts of serum albumin, insulin, transferrin, IL-3, SCF, and Epo, such as EPSFM and EPSFM+LDL. In one preferred embodiment, the pre-electroporation medium is substantially free of fatty acid sources and hydrocortisone; however, the addition of fatty acid sources such as LDLs may be desirable in some instances and it is within the capacity of a competent technician to determine when such an addition is desirable. Various post-electroporation media are suitable for use with the method of the invention, and it is within the capacity of a competent technician to select one which is appropriate. The preferred post-electroporation medium comprises EPSFM supplemented with effective amounts of LDL and a suitable plasma such as heat inactivated human plasma. The human plasma may be autologous or heterologous, and may be obtained from a variety of sources including umbilical cord blood or peripheral blood. Preferably, the plasma is obtained from the same source as the cells being electroporated. Alternatively, post-electroporation media which are substantially free of plasma and serum are known in the art and it is within the capacity of a competent technician to select such a medium.

EpoR Mutants

No constitutively active human EpoR has been previously reported. A constitutively active murine EpoR has been reported in which the C-terminus was truncated and amino acid residue 129 was mutated from R to C. The amino acid sequence in the region of the murine EpoR R129 residue is highly conserved between mice and rats, whereas the comparable region of the human EpoR shares only a 54% amino acid conservation with the murine EpoR:

```
human   P-V-G-L-V-A-R-L-A-D-E-S-G   (SEQ. ID. NO. 9)
murine  P-A-G-L-L-A-R*-R-A-E-E-G-S  (SEQ. ID. NO. 10)
rat     P-A-G-L-L-A-R-R-A-E-E-G-S   (SEQ. ID. NO. 11)
*site of R129C mutation within the murine Epo
```

Although mice and rats are closely related species, the complete conservation of the EpoR amino acid sequence in the R129 region between these species suggests that amino acid sequence is very important to the function of this region. Based on the differences in amino acid sequence between the human and murine EpoR within this critical region, it was not clear what the effect of an R to C mutation within the human EpoR would have on the function of the resultant EpoR.

It was therefore surprising that the mutation of R154 to C (corresponding to murine R129) in truncated human EpoR (at residue) resulted in the production of a constitutively active human EpoR (EpoR(R154C)). This constitutively active EpoR allows Epo-independent EpoR signaling within cells and are therefore useful in treating Epo and EpoR related conditions. A second constitutively active human EpoR is provided herein which is a full length human EpoR having a R154C point mutation.

The present invention provides mutant human EpoR's suitable for expression in human erythroid cells. These mutant EpoR's are valuable in treating and alleviating the symptoms of disorders relating to inadequate EpoR signaling in patient cells.

The hypersensitive (EpoR(t439)) and constitutively active (EpoR(R154C) and EpoR(t439;R154C)) EpoRs of the present invention may be introduced into suitable human cells using standard gene therapy methods. This allows the treatment of patients suffering as a result of Epo levels in their circulation which are insufficient to provide desirable levels of signaling by their naturally occurring EpoRs. Such patients may be treated by the introduction of constitutively active or hypersensitive EpoRs which will provide a greater extent of intracellular signaling than would be provided by the patient's naturally occurring EpoRs.

EXAMPLE 1

Expansion and Differentiation of Erythroid Cells from CD34$^+$lin$^-$ cells in Serum-free Suspension Culture CD34$^+$ cells were enriched from human umbilical cord blood LDMNC by lineage depletion of cells expressing CD3, CD14, CD16, CD19, CD24, CD56, CD66b and glycophorin A (GlyA) to enrich lin$^-$ cells. The viability of CD34$^+$ cells pre- and post-enrichment was determined by trypan-blue dye exclusion and cells were characterized for CD34 and CD45 co-expression by standard flow cytometry methods (see Table 2, FIG. 1).

TABLE 2

Viability[1] and Percentage[1] of CD34+ in Cord Blood LDMNC Before and After Lineage Depletion

| n | Viability % Before | Viability % After | CD 34+ Cells % Before | CD 34+ Cells % After | CD34+ Cell Recovery (%) |
|---|---|---|---|---|---|
| 35 | 93.6 ± 6.5 | 90.1 ± 8.1 | 1.01 ± 0.47 | 41.7 ± 15.6 | 38.3 ± 20.8 |

[1]average ± SD
n = number of experiments

CD34+ cells were cultured at an initial seeding density of $1-2\times10^4$ cells/ml in EPSFM+LDL with the composition described in Table 1B. At approximately 7-day intervals, aliquots of cultured cells were removed for measurement of viability by trypan-blue dye exclusion, for phenotypic characterization by flow cytometry, and for detection of the presence of hemoglobin (Hb) by benzidine (BZ) staining. Cells were reseeded thereafter at a density of $1\times10^5$ cells/ml in fresh culture medium. Cell expansion in EPSFM+LDL was dependent on the presence of all three recombinant growth factors, namely IL-3, SCF, and Epo, with the removal of any of these three resulting in the abrogation of cell expansion. Cells cultured in EPSFM+LDL expanded more than one million-fold in approximately 30 days. The expansion of CD34+ enriched cells was greater than that of unfractionated human umbilical cord blood LDMNC cultured in a comparable medium as depicted in FIG. 2.

Figure 3:
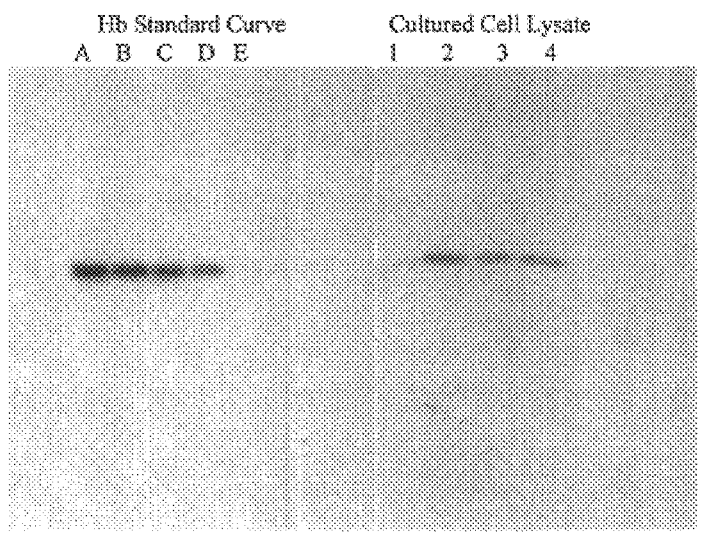
FIG. 3 depicts the results of a Western blot of lysates from CD34$^+$enriched cells cultured according to Example 1. Twenty-five uM hemin was added to some samples of both day 9 and day 17. Cells were harvested at day 17 and day 22 of culture. Cell lysates were prepared, subjected to electrophoresis through a 12% polyacryalmide gel and then transferred to a PVDF membrane. Hemoglobin standards were included for the purpose of quantification. The Western blot was probed with anti-hemoglobin antibodies and subsequently developed using chemiluminescence.

At the end of 30 days in culture cells were fully differentiated erythroid cells with 57% of the cells staining positively with benzidine and 85% of the cells expressing the erythroid-specific membrane glycoprotein glycophorin A (GlyA). Morphological analysis of Giemsa-Wright stained cells revealed the majority to be nucleated erythroblasts. Five to ten percent of the cells were enucleated reticulocytes/mature erythrocytes which is concordant with 6% of the cells expressing GlyA in the absence of CD71 (Table 3). The amount of hemoglobin per cell was determined to be 5.2 pg using Western blot analysis. (see FIG. 3). The addition of hemin to defined culture medium did not substantially increase the Hb content, the number of cells expression GlyA, or the number of cells that stained positively with BZ.

EXAMPLE 2

Figure 4:
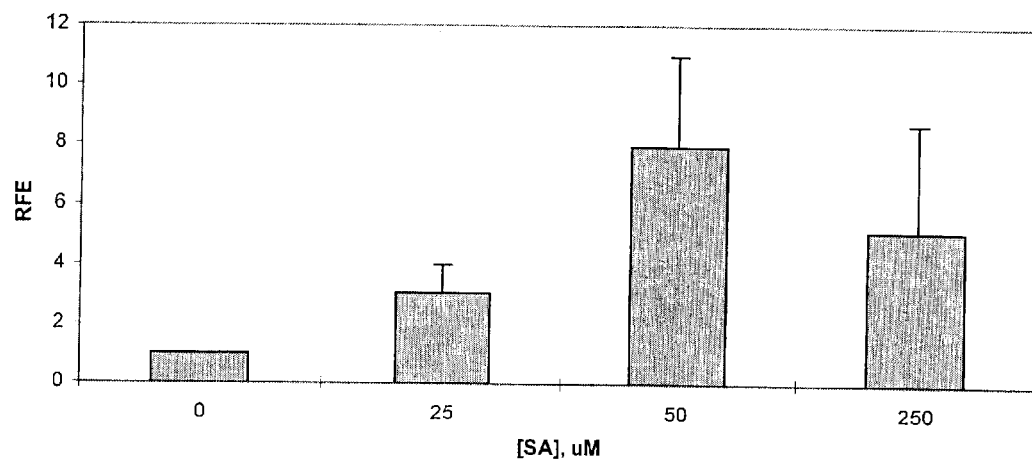
FIG. 4 is a graphical representation of data obtained in Example 2 regarding the relative fold expansions (RFE) of CD34$^+$enriched cells cultured in EPSFM+LDL with the addition of 0, 25, 50 or 250 uM SA ("heme inhibitor"). Relative fold expansions (RFE) are compared to the control sample (EPSFM+LDL +0 uM SA).
Figure 5:
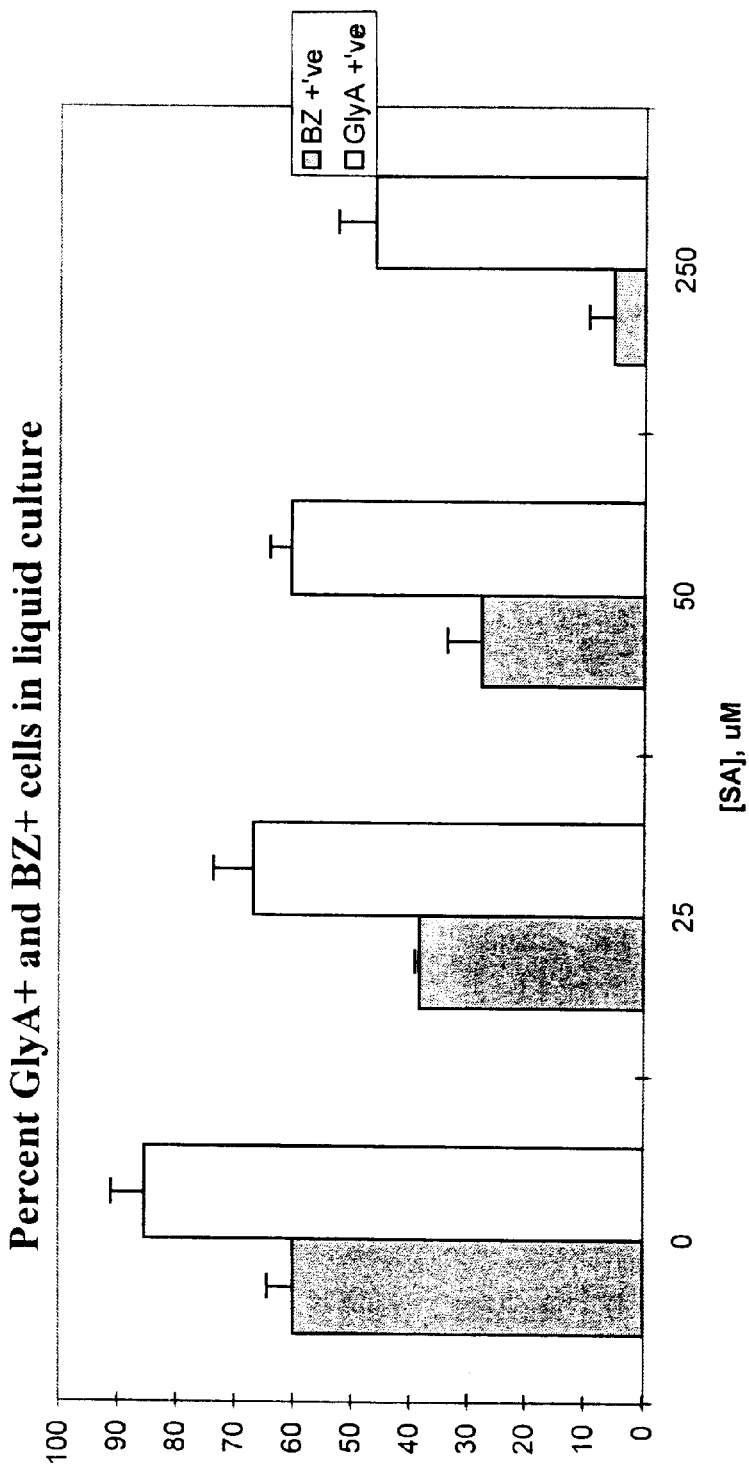
FIG. 5 is a graphical representation results obtained from Example 2, namely, the percentage of the cells that stained positively with benzidine (BZ) and were positive for the expression of GlyA (as determined by FACS analysis). Cells were cultured as described in Example 1 in EPSFM+LDL with the addition of 0, 25, 50 or 250 uM SA.
Figure 6:
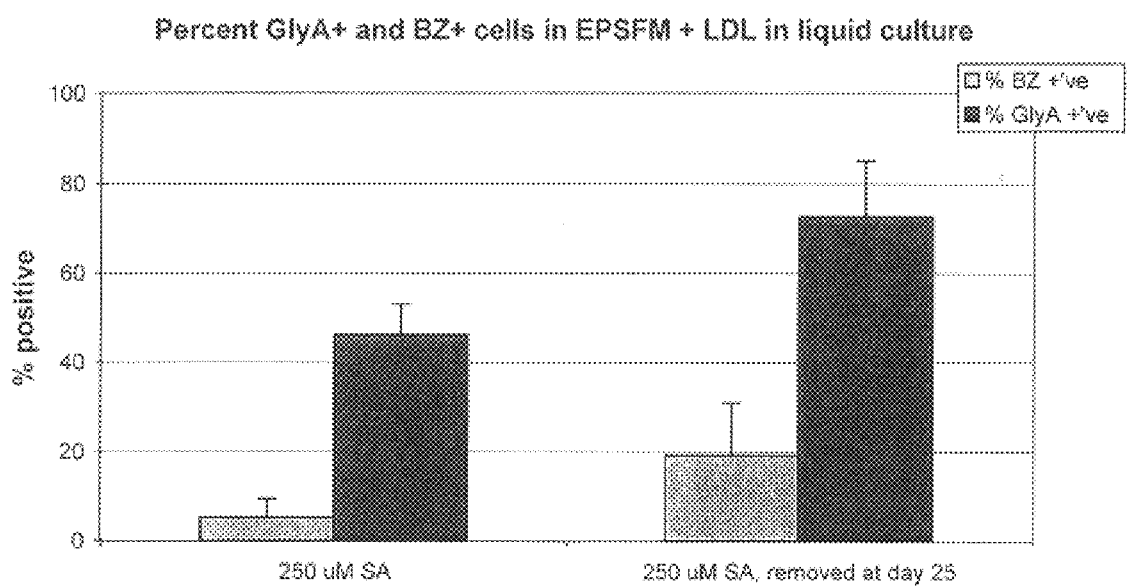
FIG. 6 is a graphical representation of results obtained from Example 2, namely, the number of cells that stained positively with benzidine (BZ) and were positive for the expression of GlyA (as determined by FACS analysis). CD34$^+$enriched cells were cultured in defined culture medium for 30 days as described in Example 1 with the addition of 250 uM SA. SA was removed from some samples after 25 days. At day 30, all samples were stained with BZ and expression of GlyA was determined by FACS.

Increased Expansion of Erythroid Cells from CD34+ Cells by the Reversible Suppression of Erythroid Differentiation CD34+ enriched cells were isolated and cultured as described in Example 1. Succinylacetone (SA), a heme synthesis inhibitor, was added to EPSFM+LDL at concentrations of 25 to 250 uM at the initiation of culture. Results are depicted in Table 4 and FIGS. 4 to 6. The addition of 50 uM SA to EPSFM+LDL increased cell expansion 8-fold when compared to controls without SA (FIG. 4). The addition of increasing amounts of SA reduced erythroid differentiation as indicated by decreasing percentages of BZ+ and GlyA+ expressing cells (FIG. 5). Maximum suppression of BZ staining and GlyA expression was achieved with 250 uM SA. When SA was removed after at least 20 days of culture, suppression of heme synthesis ceased, and the percentages of BA+ and GlyA+ cells increased significantly by the following passage (FIG. 6).

TABLE 4

Total fold expansion with the addition of 25, 50 and 250 uM SA to EPSFM + LDL

| [SA] | Total fold expansion (n = 3) |
|---|---|
| 0 | $2.27 \times 10^6$ |
| 25 uM | $6.36 \times 10^6$ |
| 50 uM | $2.89 \times 10^7$ |
| 250 uM | $6.77 \times 10^6$ |

EXAMPLE 3

Effect of LDL Removal on Erythroid Differentiation

CD34+ enriched cells were cultured in EPSFM+LDL or EPSFM by the method described in Example 1 (EPSFM has the same composition as EPSFM+LDL except that EPSFM does not contain LDLs or other sources of fatty acids.) Culture of cells in EPSFM along resulted in a slight decrease in overall erythroid cell expansion as compared to samples containing LDL (EPSFM+LDL: $3.5\times10^5$ fold expansion, compared to EPSFM: $2.0\times10^5$ fold expansion) whereas the amount of hemoglobin produced was substantially increased in the absence of LDL (from 8.8 pg per BA+cell in EPSFM+LDL to 30.7 pg per BZ+cell in EPSFM). The removal of LDL did not affect the expression of GlyA of CD71 (Table

TABLE 3

Summary of the growth and differentiation of CD34+ enriched cells in EPSFM + LDL

| | FE | Max. BZ | Culture duration in days | pg Hb/ cell | % GlyA | FACS analysis (maximum values) % GlyA/CD71 | % CD 71 |
|---|---|---|---|---|---|---|---|
| mean (± % CV) | 1,452,931 ± 144% | 57 ± 25% | 31 ± 11% | 5.2 ± 65% | 85.4 ± 15.8% | 79.6 ± 17.0% | 92.0 ± 5.0% |
| range | 202,438– 6,188,108 | 20–72 | 25–38 | 2.1–12.0 | 44.5–97.7 | 43.6–95.6 | 81.6–95.8 |
| median | 429,764 | 61 | 30 | 4,1 | 86.2 | 80.5 | 94.3 |

%CV = coefficient of variations

5). The overall (mean) Hb per cell in EPSFM cultured populations (9.5 g/cell) was more than double that observed in EPSFM+LDL cultured cells (4.1 pg/cell). Thus, despite the slightly ower overall cell expansion observed in EPSFM cultures, EPSFM is a more efficient culture medium than EPSFM+LDL for the production of Hb.

TABLE 5

Fold expansion, percentage of cells BZ, GlyA and CD71 positive and Hb content of cells cultured in EPSFM + LDL

|  | EPSFM + LDL (±SD) | EPSFM no LDL (±SD) |
|---|---|---|
| fold expansion | $3.5 \times 10^5 \pm 2.5 \times 10^5$ | $2.0 \times 10^5 \pm 1.5 \times 10^5$ |
| maximum BZ + cells (%) | 40 ± 13 | 36 ± 16 |
| GlyA$^+$(%) | 84 ± 2 | 83 ± 8 |
| CD71$^+$/GlyA$^+$(%) | 81 ± 5 | 79 ± 10 |
| CD71$^+$(%) | 94 ± 6 | 93 ± 9 |
| Hb/BZ + cell (pg) | 8.8 | 30.7 |
| Hb/cell (pg) | 4.1 | 9.5 |

EXAMPLE 4

Increased Gene Transfer Efficiency by Electroporation of Erythroid Cells

4A. Electroporation of freshly isolated CD34$^+$ enriched cells

Freshly isolated CD34$^+$ enriched cells, prepared as described in Example 1, were washed in electroporation buffer (EB) (composed of D-PBS plus 11 mM glucose) and resuspended in EB to a density of between $5.0 \times 10^6$ and $1.3 \times 10^7$ cells/ml. Cells were placed on ice for 10 minutes prior to electroporation. Immediately prior to electroporation, supercoiled plasmid DNA (or an equivalent volume of D-PBS) was added to the cell sample to a final concentration of 50 ug/ml. Cells were electroporated by standard means using the conditions described in Table 6. Immediately after electroporation, cells were placed in recovery media (RM) comprising EPSFM+LDL plus 5% pooled human umbilical cord blood plasma, and placed on ice for a further 10 minutes. Cells were then incubated at 37° C. for 18 to 24 hours, after which samples were washed in wash buffer (WB), comprising PBS with 1% BSA and 0.1% sodium azide, pH 7.2). Transfection efficiency was measured using either the reporter plasmid pGREENLANTERN™ (which contains the gene coding for green fluorescent protein (GFP) from the *Aequorea victoria* jellyfish with a codon sequence "humanized" for efficient translation in human cells and transcribed from the CMV immediately early enhancer/promoter) or the pEGFP plasmid (which contains the GFP gene, human codon-optimized and containing a chromophore mutation which produces fluorescence 35 times more intense than wild-type GFP also transcribed from the CMV promoter). Cells were resuspended in 0.5 ml of WB and analyzed by flow cytometry for the expression of the GFP gene on an Coulter Epics Elite FACScan using forward and side scatter and fluorescence intensity in the fluorescein isothiocyanate (FITC) band pass (excitation at 488 nm/absorption at 525 nm). The transfection efficiency was determined as the percentage of GFP positive cells in transfected samples minus the percentage of positive cells in the mock transfected sample. Electroporated freshly isolated CD34$^+$ cells were transfected to a maximal efficiency of 2.7% (see Table 6).

TABLE 6

Electroporation of freshly isolated CD34 cells from umbilical cord blood using pGREENLANTERN and pEGFP

| Cells | Gene | Pulse width (uF) | E-field (kV/cm) | % Green |
|---|---|---|---|---|
| fresh CD34$^+$ cells | pGREENLANTERN n = 1 | 1.46 | 6.0 | 2.7 |
|  | EGFP n = 1 | 1.36 | 10.0 | 0.9 |
|  | EGFP n = 1 | 4.80 | 2.0 | 0.9 | n = number of experiments

4B. Electroporation of CD34$^+$ enriched cells cultured in defined culture medium CD34$^+$ enriched cells were cultured for 7 to 11 days, as described in Example 1. At that time, cultures has expanded approximately 93 fold and were partially erythroid with 41% expressing GlyA on the cell surface and 16% staining positive with BZ. Fewer than 2% of the cells expressed CD34, and hematopoietic progenitors were present at a frequency of 21 BFU-E, 33 CFU-E and 25 CFU-GM per $1 \times 10^5$ cells as detected in methylcellulose colony forming assay. Cells were washed in EB and subjected to electroporation at various voltages as described above. Field strength, capacitance, and pulse width were optimized to achieve an average transfection efficiency of approximately 20% as measured at 24 hours post-electroporation. Cells transfected at field strengths higher or lower than 5.0 kV/cm resulted in a decrease in transfection efficiency (Table 7).

TABLE 7

Transient transfection efficiencies of cultured erythroid cells as a function of field strength using the reporter gene pGREENLANTERN

| # of experiments | Culture duration (days ± SD) | Field strength (kV/cm) | pulse width (msecs ± SD) | GFP positive at 24 hours (% ± SD) |
|---|---|---|---|---|
| 13 | 8 ± 3 | 5.0 | 1.43 ± 0.04 | 20.1 ± 9.2 |
| 3 | 11 ± 3 | 2.5 | 1.85 ± 0.30 | 5.2 ± 8.5 |
| 3 | 12 ± 3 | 6.0 | 1.24 ± 0.26 | 10.4 ± 15.4 |

SD = standard deviation

EXAMPLE 5

CD34$^+$ Cells Cultured in EPSFM+LDL+SA are Readily Electroporatable

CD34$^+$ enriched cells were cultured in EPSFM+LDL in the presence of either 50 uM or 250 uM SA as for 10–11 days described in Example 2. Cells were electroporated as described in Example 4 at 5.0 kV/cm in the presence of either of two plasmids, namely: pGREENLANTERN or EGFPiresNEO®. Cells cultured in EPSFM+LDL+SA prior to electroporation were readily transfected at a frequency of 16% and 10% as assessed by pGREENLANTERN and EGFPiresNEO® respectively.

EXAMPLE 6

Design of a Constitutively Active Human EpoR

Full length and truncated human EpoR complimentary DNAs (cDNAs) were isolated from human umbilical cord blood LDMNC using standard polymerase chain reaction methods. RNA was initially extracted from cord blood LDMNC using the acid guanidinium thiocyanate—phenol—chloroform extraction protocol (Chomczymski (1987) Anal. Biochem. 162: 156). First strand cDNA was made from the RNA using reverse transcriptase. A full length EpoR cDNA was amplified using the 5' EpoR (5'GGAAGCTTATGGACCACCTCGGGGCG) (SEQ ID NO.1) and 3' EpoR (5'GCTCTAGACTAAGAGCAAGCCACATAGCT) (SEQ ID NO 2) primers. A truncated EpoR cDNA was amplified using the 5' EpoR and 3' trunEpoR (5'GCTCTAGACTATGGACGCAAGAGCTGGGA) (SEQ. ID NO.3) primers. The 3' trunEpoR primer was designed to replace Trp439 (relative to the initiation Met) with a stop codon (TAG). The amplified cDNAs were isolated and subcloned into the pBluescript® SK phagemid for sequence verification of the resultant truncated EpoR (EpoR(t439) (SEQ.ID.NOS. 4 and 5, FIG. 9A(cDNA), and FIG. 9B(amino acid)).

The truncated EpoR (EpoR(t439)) cDNA was subsequently subcloned into the pALTER®-1 vector for site-directed mutagenesis and single-stranded DNA was isolated. Mutagenesis of Arg154 (relative to the initiation Met) to Cys was conducted by hybridizing the R154C primer (5' CTCGTCAGCCAAGCATGCCACCAGCCCC) (SEQ.ID.NO. 8) to the single-stranded DNA. The primer was extended and the nick sealed using DNA polymerase and ligase respectively. The double stranded plasmid was transformed initially into ES1301 mutS bacteria (mismatch repair minus strain) then subsequently into JM109 bacteria. The R154C mutation was confirmed through standard sequence analysis. The cDNA and amino acid sequence of the R154 mutant EpoR(t439) ("EpoR(t439;R154C") is depicted in SEQ.ID.NOS. 6 and 7, and FIG. 10A (cDNA) and B (amino acid).

Figure 7:
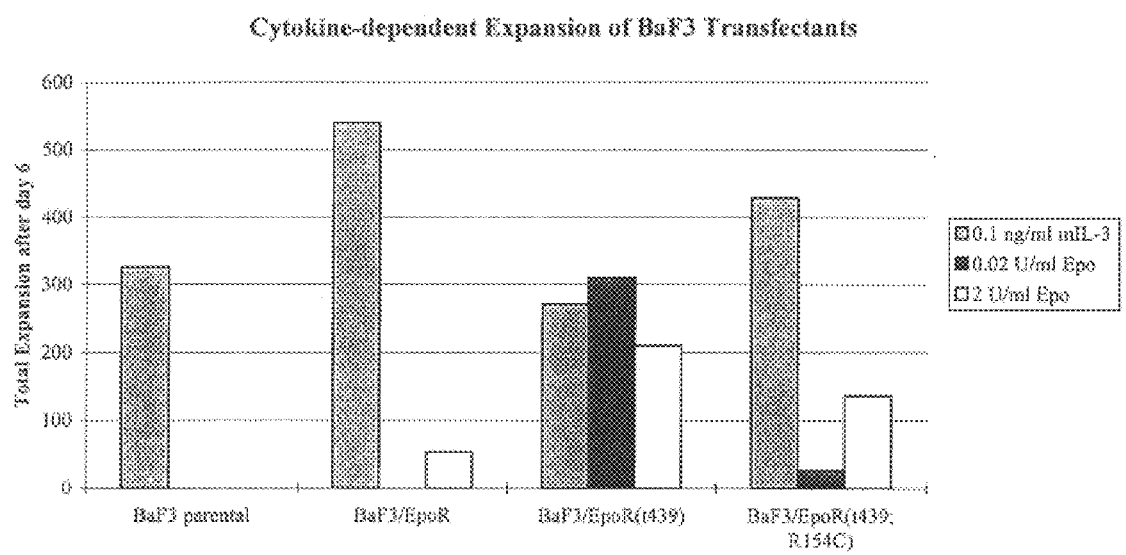
FIG. 7 is a graphical representation of results obtained from Example 6, namely, the total cell expansion after 6 days of parental BaF3 cells, BaF3 cells transfected with EpoR, EpoR(t439) or EpoR(t439; R154C) when cultured in RPMI with 10% FBS and either 0.1 ng/ml, 0.02 U/ml Epo or 2 U/ml Epo as described in Example 6.

The functionality of the EpoR(t439; R154C) was tested and compared to the wild-type EpoR (wtEpoR) and EpoR (t439) using the BaF3 cell line. The cDNAs encoding these three different EpoRs were subcloned into the pcDNA3.1 expression vector, which provides high-level constitutive expression of proteins in mammalian cells and also contains the neomycin gene for the selection of stable transfectant with G418. The vector constructs were electroporated into BaF3 cells and stable transfectants were isolated in the presence of 600 ug/ml G418. BaF3 transfectants were maintained in RPMI-1640 with 10% FBS and 5% WEHI conditioned medium (a source of murine IL-3), except during the cytokine-dependency studies when cells were maintained in RPMI-1640 plus 10% FBS, along with the indicated cytokines. Growth of the different EpoR transfectants in the presence of either murine IL-3 or two different doses of Epo was compared to that of the parental (non-transfected) BaF3 cells (FIG. 7). The parental BaF3 cells did not grow in the absence of murine IL-3. The BaF3/EpoR transfectants grew in the presence of 2 U/ml Epo alone; however, this growth was less than was seen with 0.1 ng/ml mIL-3. These cells did not grow in 0.02 U/ml Epo. The BaF3/EpoR(t439) transfectants grew equally well in either 0.1 ng/ml mIL-3 or 0.02 or 2 U/ml Epo. Thus, the EpoR(t439) is functional and hypersensitive to Epo. The BaF3/EpoR(t439; R154C) transfectants grew in the presence of either 0.02 or 2 U/ml Epo but less than in the presence of IL-3. All three EpoR constructs encode functional receptors that allow expansion of the BaF3 cells in the presence of Epo without exogenous IL-3.

Figure 8:
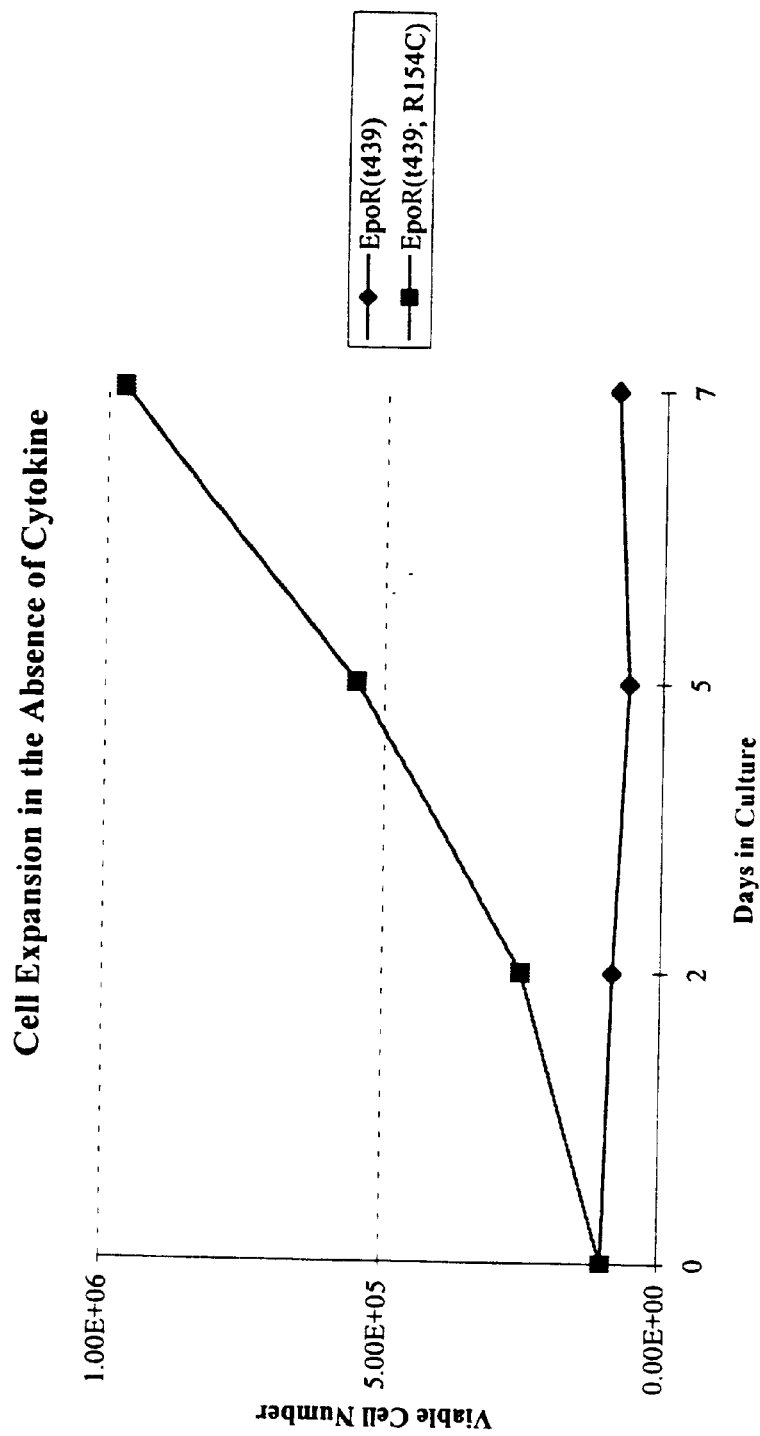
FIG. 8 is a graphical representation of results obtained from Example 6, namely, growth of BaF3 cells transfected with either EpoR(t439) and EpoR(t439; R154C) as described in Example 6.

The EpoR(t439) and EpoR(t439; R154C) transfectants were also cultured in the absence of exogenous cytokines to determine whether EpoR(t439; R154C) encoded a constitutively active form of the EpoR. The EpoR(t439; R154C) supported expansion of the BaF3 cells in the absence of exogenous cytokines whereas the EpoR(t439) did not support cell expansion under these conditions. Thus, the EpoR (t439; R154C) is a constitutively active form of the EpoR (FIG. 8).

EXAMPLE 7

Transfection of EpoR(t439; R154C) into Erythroid-cultured CD34+ Cells Increases the Survival of Erythroid Progenitors CD34+lin− cells cultured for 7 to 10 days in EPSFM+LDL were washed in EB and subjected to electroporation in the presence of EpoR(t439; R154C)/pcDNA3.1 expression vector as described in Example 3. Two to three days post-transfection, aliquots of untransfected and EpoR(t439; R154C)/pcDNA3.1 transfected cells were counted for viability by trypan-blue dye exclusion and methylcellose colony-forming assays were performed in IMDM, 1% methylcellulose, 30% FBS, 1% BSA, $10^{-4}$ M β mercaptoethanol, and 2 µM glutamine, IL-3 (10 ng/ml), SCF (50 ng/ml) and EPO (2 U/ml). Cell populations expressing of the EpoR(t439; R154C)/pcDNA3.1 had an increase in erythroid colony number over that obtained by untransfected cell populations (Table 8)

Cells transfected with either EpoR(t439; R154C)/pcDNA3.1 or the pcDNA3.1 vector alone were placed in liquid culture (IMDM, 1% BSA, 10 ng/ml rhIL-3, 50 ng/ml SCF and 2 U/ml EPO) in the presence of 500 ug/ml G418 for 14 days. At this time, cells were counted for viability by trypan-blue dye exclusion and methylcellose colony-forming assays were performed in IMDM, 1% methylcellulose, 30% FBS, 1% BSA, $10^{-4}$ M β mercaptoethanol, and 2 µM glutamine, IL-3 (10 ng/ml), SCF (50 ng/ml), EPO (2 U/ml) and 500 ug/ml G418. More erythroid colonies were detected in samples transfected with plasmid DNA containing EpoR(t439; R154C) than with those transfected with plasmid DNA (pcDNA3.1 vector) alone (Table 9). No colonies were detected in the untransfected or "mock" transfected controls. Thus, expression of the EpoR(t439; R154C)/pcDNA3.1 plasmid not only conferred G418 resistance but increased the number of erythroid progenitors detectable after 14 days of liquid culture.

TABLE 8

Number of Erythroid colonies[1] after Transfection of Cultured Erythroid Cells with EpoR(t439; R154C)

| Experiment # | # of erythroid colonies in control[2] samples | # of erythroid colonies in EpoR(t439; R154C) transfected samples | increase in erythroid colonies |
|---|---|---|---|
| 1 | 48 | 428 | +388 |
| 2 | 424 | 522 | +98 |
| 3 | 0 | 66 | +66 |

[1]BFU-E and CFU-E
[2]untransfected or mock transfected

TABLE 9

Number of Erythroid colonies[1] after Transfection of Cultured Erythroid Cells with EpoR(t439; R154C) and Expansion in Liquid Culture for 14 Days with G418

| | Erythroid colonies/ $1 \times 10^5$ cells |
|---|---|
| pcDNA3.1 | 13 |
| EpoR(t439; R154C) | 45 |

[1]BFU-E and CFU-E

EXAMPLE 8

The Addition of SA and Hemin at Day 15 of Culture Enhances Hb Content of Culture

CD34$^+$ enriched cells were isolated and cultured in EPSFM+LDL as described in Example 1. In some samples, SA was added to EPSFM+LDL to a final concentration of 25 uM. In some instances, hemin was added to the SA containing cultures to a final hemin concentration of 25 uM. Hemin was added to some SA containing cultures at the initiation of culture and to others after 15 days of culture. The addition of SA, an inhibitor of heme synthesis, to EPSFM+LDL increased the fold expansion of cells obtained but reduced the percentage of GlyA$^+$ cells and the Hb content of these cells (Table 10). The low hemoglobin content was ameliorated by the addition of hemin to EPSFM+LDL+SA at the initiation of culture. However, as the percentage of GlyA$^+$ cells was decreased in this instance, the total amount of Hb per culture is similar to that observed with culture in EPSFM+LDL alone. The addition of hemin after 15 days of culture, instead of at culture initiation, further increased the fold expansion without reducing the percentage of GlyA$^+$ cells. Unexpectedly, the amount of hemoglobin per cell increased to approximately that obtained with EPSFM+LDL. This timing of SA withdrawal and hemin addition resulted in an overall 7 fold increase in the amount of Hb produced per culture in addition to an increase in the total number of GlyA$^+$ cells.

TABLE 10

| | At Culture Termination | | | | |
|---|---|---|---|---|---|
| Addition to EFSFM + LDL | Total number of cells | % GlyA positive cells | Total number of GlyA$^+$ cells | Hb per GlyA$^+$ cell | Total Hb per culture |
| * | $6.9 \times 10^9$ | 92 | $6.4 \times 10^9$ | 16.1 pg/cell | 0.1 g |
| SA | $3.9 \times 10^{10}$ | 74 | $2.9 \times 10^{10}$ | 0.95 pg/cell | 0.03 g |
| SA + hemin | $6.1 \times 10^{10}$ | 46 | $2.8 \times 10^{10}$ | 3.91 pg/cell | 0.1 g |
| SA + hemin @ t15 | $7.8 \times 10^{10}$ | 52 | $4.3 \times 10^{10}$ | 15.8 pg/cell | 0.7 g |

The entire disclosures of Canadian Appln Nos. 2241576 and 2260332, filed Jun. 25, 1998 and Jan. 25, 1999, are hereby incorporated by reference.

We claim:

1. A method of producing an expanded population of erythroid cells comprising culturing an initial population containing erythroid precursors in a serum free defined medium essentially free of fatty acids and hydrocortisone comprising effective amounts of: serum albumin, insulin, transferrin, IL-3, SCF, SA and Epo and recovering an expanded population of erythroid cells.

2. A method of producing a differentiated population of erythroid cells comprising culturing an initial population containing erythroid precursors in a serum free defined medium essentially free of fatty acids and hydrocortisone comprising effective amounts of: serum albumin, insulin, transferrin, IL-3, SCF, SA and Epo and recovering a differentiated population of erythroid cells.

3. A method of enhancing the expansion and differentiation of a population of erythroid cells comprising:
   (a) culturing an initial population comprising erythroid precursors in a suitable erythroid cell culture medium in the presence of SA, and
   (b) adding an effective amount of a heme source.

4. The method of claim 3 wherein the heme source is hemin.

5. The method of claim 3 wherein the heme source is Hb.

6. The method of claim 3 wherein the erythroid cell culture medium is EPSFM+LDL.

7. The method of claim 3 wherein the erythroid cells are derived from a human.

8. A method of producing exogenous protein in erythroid cells comprising:
   (a) culturing an initial cell population in a serum free defined culture medium comprising effective amounts of serum albumin, insulin, transferrin, IL-3, SCF, Epo, SA and LDLs,
   (b) electroporating cells in the presence of exogenous DNA, encoding said protein
   (c) allowing cells to recover in an appropriate post-electroporation medium,
   (d) screening the electroporated cells for exogenous protein expression,
   (e) culturing cells of step (d) which express exogenous protein and
   (f) recovering the protein from the cells of step (e).

9. The method of claim 8 wherein the foreign source protein is a globin protein.

10. The method of claim 8 wherein the foreign source protein is a transcription factor.

11. The method of claim 8 wherein the foreign source protein is an immortalizing protein.

12. The method of claim 8 wherein the foreign source protein is a genetically altered growth factor receptor.

13. A human EpoR having an R→C mutation at amino acid residue 154 and truncated at amino acid residue 439 and having the amino acid sequence shown in SEQ. ID. NO.7.

14. An erythroid cell expressing the EpoR of claim 13.

15. A method of enhancing the expansion of a population of erythroid cells comprising culturing an initial population comprising erythroid precursors in a suitable erythroid cell culture medium in the presence of SA.

* * * * *

UNITED STATES PATENT AND TRADEMARK OFFICE
CERTIFICATE OF CORRECTION

PATENT NO. : 6,361,998 B1
DATED : March 26, 2002
INVENTOR(S) : David N. Bell, Kathryn Emma Matthews and Susan G. Mueller It is certified that error appears in the above-identified patent and that said Letters Patent is hereby corrected as shown below:

Column 4,
Lines 53 and 55, replace "imitation" by -- initiation --;

Column 7,
Line 62, replace "charactoristics" by -- characteristics --;

Column 8,
Lines 3, 23 and 52, replace "charactoristics" by -- characteristics --;

Column 9,
Line 12, replace "charactoristics" by -- characteristics --;

Column 12,
Line 56, replace "differ/source" by -- differ --;

Column 13,
Line 15, replace "pa-1-" by -- pv.1 --;
Line 27, replace "bel-Z ans qmv" by -- bcl-2 and amv --;
Line 38, replace "Piaoetal" by -- Piao et al --;

Column 18,
Lines 19 and 48, replace "Ba+" by -- BZ+ --;

Signed and Sealed this

Twenty-ninth Day of April, 2003

JAMES E. ROGAN
*Director of the United States Patent and Trademark Office*